(12) United States Patent
Barkol et al.

(10) Patent No.: US 11,031,139 B2
(45) Date of Patent: Jun. 8, 2021

(54) SYSTEMS AND METHODS FOR CONVERSATIONAL FLEXIBLE DATA PRESENTATION

(71) Applicant: General Electric Company, Schenectady, NY (US)

(72) Inventors: Omer Barkol, Haifa (IL); Renato Keshet, Haifa (IL); Andreas Tzanetakis, Schenectady, NY (US); Constance Anne Rathke, Nixa, MO (US); Reuth Goldstein, Haifa (IL); Michelle Townshend, Traverse City, MI (US)

(73) Assignee: General Electric Company, Schenectady, NY (US)

( * ) Notice: Subject to any disclaimer, the term of this patent is extended or adjusted under 35 U.S.C. 154(b) by 141 days.

(21) Appl. No.: 16/271,546

(22) Filed: Feb. 8, 2019

(65) Prior Publication Data

US 2020/0258511 A1    Aug. 13, 2020

(51) Int. Cl.
*G10L 15/22*    (2006.01)
*G16H 10/60*    (2018.01)
(Continued)

(52) U.S. Cl.
CPC ........... *G16H 80/00* (2018.01); *G06F 16/338* (2019.01); *G06F 40/295* (2020.01); *G06F 40/30* (2020.01);
(Continued)

(58) Field of Classification Search
CPC ... G10L 15/22; G10L 15/063; G10L 15/1815; G10L 15/16; G10L 2015/223;
(Continued)

(56) References Cited

U.S. PATENT DOCUMENTS 9,536,049 B2 *   1/2017  Brown .................... G06F 3/167
2002/0152202 A1* 10/2002  Perro .................. G06F 16/3334
(Continued)

FOREIGN PATENT DOCUMENTS

WO        2013036677 A1     3/2013
WO   WO-2013036677 A1 *    3/2013   ............. G06Q 10/00

OTHER PUBLICATIONS

International Application No. PCT/US2020/016753 filed Feb. 5, 2020—International Search Report and Written Opinion dated May 11, 2020; 14 pages.

*Primary Examiner* — Edwin S Leland, III
(74) *Attorney, Agent, or Firm* — McCoy Russell LLP

(57) ABSTRACT

Systems and methods are provided for presenting aggregate data in response to a natural language user input. In one example, a system includes a display and a computing device coupled to the display and storing instructions executable to receive a natural language user input, process the natural language user input, in response to determining that the user input includes a request to display two different plots of record data specific to the subject, generate, with the virtual assistant, a single graph including the two different plots of record data based on the processed natural language user input, the two different plots of record data plotted from two different record data sets, one or more aspects of the single graph selected based on an overlapping parameter for each of the two different record data sets, and output, to the display, the single graph as part of a communication thread.

20 Claims, 15 Drawing Sheets

(51) Int. Cl.
*G06N 20/00* (2019.01)
*G10L 15/06* (2013.01)
*G10L 15/16* (2006.01)
*G10L 15/18* (2013.01)
*G06F 3/16* (2006.01)
*G06F 40/30* (2020.01)
*G16H 80/00* (2018.01)
*G06F 16/338* (2019.01)
*G06F 40/295* (2020.01)

(52) U.S. Cl.
CPC ........ *G10L 15/063* (2013.01); *G10L 15/1815* (2013.01); *G10L 15/22* (2013.01); *G16H 10/60* (2018.01); *G06N 20/00* (2019.01); *G10L 15/16* (2013.01)

(58) Field of Classification Search
CPC ........ G06F 40/30; G06F 40/295; G06F 3/165; G06F 16/338; G16H 10/60; G16H 80/00; G06N 20/00

USPC ........................................ 704/232
See application file for complete search history.

(56) References Cited

U.S. PATENT DOCUMENTS

| | | | |
|---|---|---|---|
| 2003/0078766 A1* | 4/2003 | Appelt | G06F 16/3344 704/9 |
| 2004/0088158 A1* | 5/2004 | Sheu | G06F 16/24522 704/9 |
| 2014/0249830 A1* | 9/2014 | Gallopyn | G16H 50/20 705/2 |
| 2016/0350488 A1* | 12/2016 | Stocker | G16H 10/60 |
| 2016/0371441 A1* | 12/2016 | Day | G16H 40/20 |
| 2017/0039336 A1* | 2/2017 | Bitran | G16H 20/70 |
| 2018/0005418 A1* | 1/2018 | Kim | G06T 11/206 |
| 2020/0013411 A1* | 1/2020 | Kumar | G10L 17/24 |
| 2020/0258511 A1* | 8/2020 | Barkol | G06F 40/30 |
| 2020/0294642 A1* | 9/2020 | Bostic | G06Q 40/08 |

\* cited by examiner

SYSTEMS AND METHODS FOR CONVERSATIONAL FLEXIBLE DATA PRESENTATION

FIELD

Embodiments of the subject matter disclosed herein relate to natural language processing of natural language user input via a user interface for flexible presentation of aggregate information.

BACKGROUND

Acute care of patients in a hospital or other medical facility may be carried out with multiple care providers per patient and may include multiple patient monitoring devices monitoring each patient. Thus, to ensure a rapid response should a patient's condition deteriorate, near-continuous monitoring of the output from the multiple monitoring devices may be necessary. Further, coordination of patient care among all the care providers may be complicated or time-consuming, further stretching care provider resources. Additionally, the presentation of patient medical information to the care providers may require multiple time-consuming and cumbersome requests or searches for information.

BRIEF DESCRIPTION

In one embodiment, a system includes a display and a computing device operably coupled to the display and storing instructions executable to output, to the display, a subject-specific communication thread including communication among a virtual assistant and one or more professionals interacting with a subject. The instructions are further executable to receive a natural language user input, input via text or voice and process, with the virtual assistant, the natural language user input to determine a user request. The instructions are executable to, in response to determining that the user request includes a request to display at least two different plots of record data specific to the subject, generate, with the virtual assistant, a single graph including the at least two different plots of record data based on the processed natural language user input, the at least two different plots of record data plotted from at least two different record data sets, one or more aspects of the single graph selected based on an overlapping parameter for each of the at least two different record data sets, and output, to the display, the single graph as part of the communication thread.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
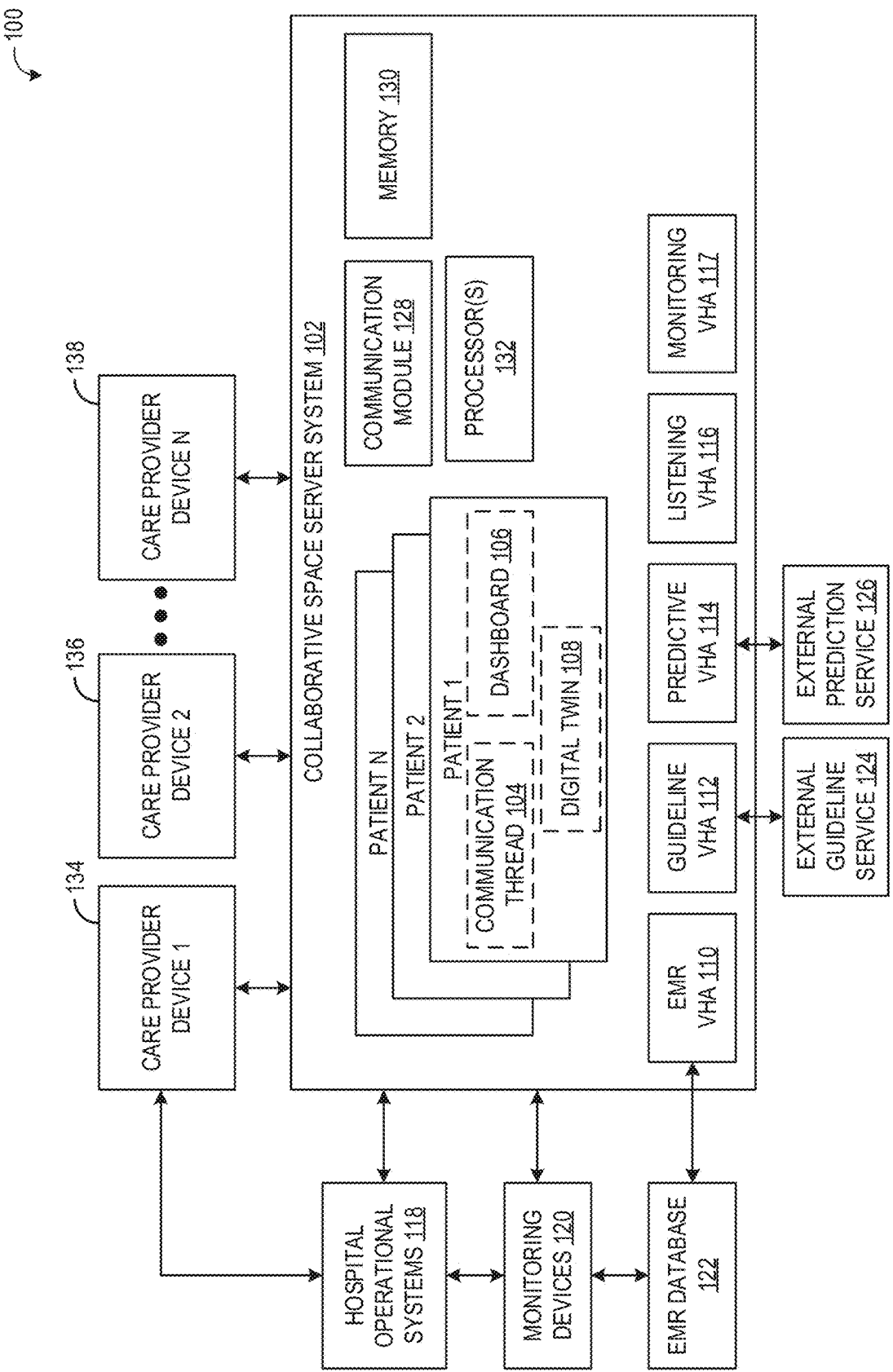
FIG. 1 schematically shows an example collaborative healthcare system.

The following description relates to various embodiments of a collaborative healthcare system that facilitates communication among care providers of a patient (which may be collectively referred to as a care provider team) and also utilizes machine and/or other deep learning models (e.g., in the form of virtual healthcare assistants) to perform certain patient monitoring and diagnostic activities. The collaborative healthcare system includes patient-specific communication channels that include communication thread-dashboard pairs to facilitate communication among the care providers and virtual healthcare assistants (also referred to as bots) on the communication thread while also graphically providing relevant patient care information (current vital signs, trends, medical history, etc.) to the care providers via the dashboard and/or communication thread.

The virtual healthcare assistants may function as information retrievers, data monitors, predictors, and more to assist the care providers. The virtual healthcare assistants may provide requested patient data (e.g., fetch data from an electronic medical record), detect changes in patient state and alert the care providers of the changed state (e.g., by detecting that a patient vital sign has reached a condition relative to a threshold), and provide care guidelines, suggested diagnostic tests, and diagnoses to the care providers. The virtual healthcare assistants may be trained to communicate using natural language including medical language, thereby allowing for care providers to communicate with the virtual healthcare assistants in the same manner as other care providers.

Each communication channel may be specific to a given patient in a given acute care facility or other medical facility or healthcare setting (e.g., hospital, urgent care facility, or nursing home). A communication channel may be initiated upon admission of the patient to the medical facility. Each care provider of the patient may be joined to the communication channel, thereby allowing collaboration and communication among all care providers (e.g., doctors, nurses, and/or specialists such as radiologists) of the patient. The one or more virtual healthcare assistants may also be joined to the communication channel. Communication occurring on the communication channel may be in the form of text messages, rich media, and/or other forms, thereby allowing care providers to view graphs of patient medical trends, medical images, and so forth. Messages sent and received on the communication channel may be saved at a central location as a communication thread, allowing care providers to access prior conversations on the channel. For example, if a virtual healthcare assistant detects a change in a patient condition that indicates potential health issues, such as high blood pressure, the virtual healthcare assistant may note the high blood pressure and alert the care provider(s) via the communication thread. The blood pressure may be displayed via the patient dashboard along with the alert. A care provider may view the blood pressure measurement by selecting the alert in the communication thread. Later, the care provider may select a graphical display of the alert in the dashboard in order to launch the portion of the communication thread in which the blood pressure alert was issued.

The dashboard and communication thread may be viewable from a variety of client devices, including but not limited to a provider client device (such as a monitor in a nurse's station) and a provider mobile device (such as a tablet or smart phone). Thus, care providers may have access to relevant data and assistance from the virtual healthcare assistants from virtually any allowed location within the medical facility, and even off-site locations in some examples.

Further, the collaborative healthcare system described herein may facilitate flexible presentation of aggregate patient medical information, to enable care providers to review multiple, different pieces of medical data related to a patient with a single request. For example, a care provider may request, using natural language that is input via the communication thread, to view two, three, or more different patient medical parameters, such as heart rate, blood pressure, blood oxygen level, etc., over time. A virtual healthcare assistant may process the natural language input to determine the user request and then generate a single graph plotting each different patient medical parameter. The virtual healthcare assistant may generate the single graph by obtaining each data set for each requested medical parameter from the patient's electronic medical record and plotting the data sets onto the single graph that is then output for display via the communication thread. To ensure the data that is plotted on the graph is displayed with sufficient clarity, the virtual healthcare assistant may plot the data based on one or more overlapping parameters (such as time, event succession, or other parameter), adjust one or more scales of the data, remove some data points that fall outside the overlapping parameter, or perform other actions with the data plots in order to fit the data on the single graph in a readable manner. In some examples, such as when three or more different medical parameters are requested, the virtual healthcare assistant may generate more than one graph and then output both graphs for display via the communication thread.

In another example, a care provider may request, using natural language that is input via the communication thread, to view a summary of a patient medical condition, such as a pain summary, fever summary, etc. A virtual healthcare assistant may process the natural language input to determine the user request and then generate a list of patient medical parameters that are associated with the patient medical condition. The list of patient medical parameters may include currently monitored patient vital signs, medicine that has been administered to the patient, diagnostic imaging results for the patient (e.g., x-ray results), care provider-driven patient state assessments (e.g., alertness, skin color), lab test results, and so forth, each related to the patient medical condition. The virtual healthcare assistant may retrieve each patient medical parameter from the patient's electronic medical record, assemble the list, and then output the list for display via the communication thread.

In each of the above examples of the displayed aggregate medical information (e.g., the single graph of multiple plots of different medical data and the summary of the patient medical condition), each individual piece of medical information that is included in the displayed aggregate medical information may be individually viewable via various interfaces, such as via the communication thread, via the dashboard, and/or via a traditional care provider interface to the patient's electronic medical record. However, by providing the ability to present all of the medical information requested by the care provider in an aggregate form, the desired medical information may be presented with only a single request from the care provider, which may reduce the time required to view the medical information versus navigating through multiple menu layers/search inputs to view all of the desired information individually. Further, even though the medical information may be individually viewable via the other interfaces disclosed above, additional insight into the patient's condition may be missed if the care provider has to view separate graphs of the patient medical parameters. For example, if a care provider were to view individual graphs of heart rate and medication administration timing, the care provider may not realize that the patient's heart rate correlates with the timing of when the medication is administered. By providing a single graph of multiple plots of different medical data, correlation between different medical parameters/events may be more easily detected, while reducing user effort required to access the information. Further, the dashboard, where some but not all possible patient medical information may be viewed, may remain easy to navigate and view by limiting the information that may be viewed via the dashboard while still providing care providers the ability to access desired information via the communication thread.

Figure 2:
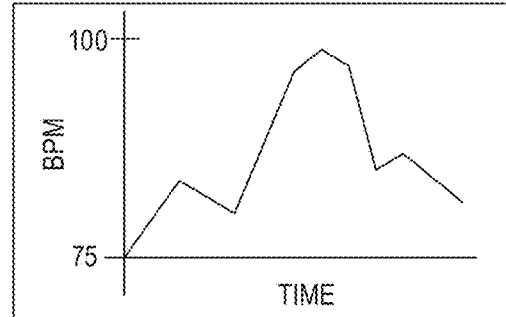
FIG. 2 shows an example display device displaying a communication thread occurring on a communication channel of the collaborative healthcare system.
Figure 3:
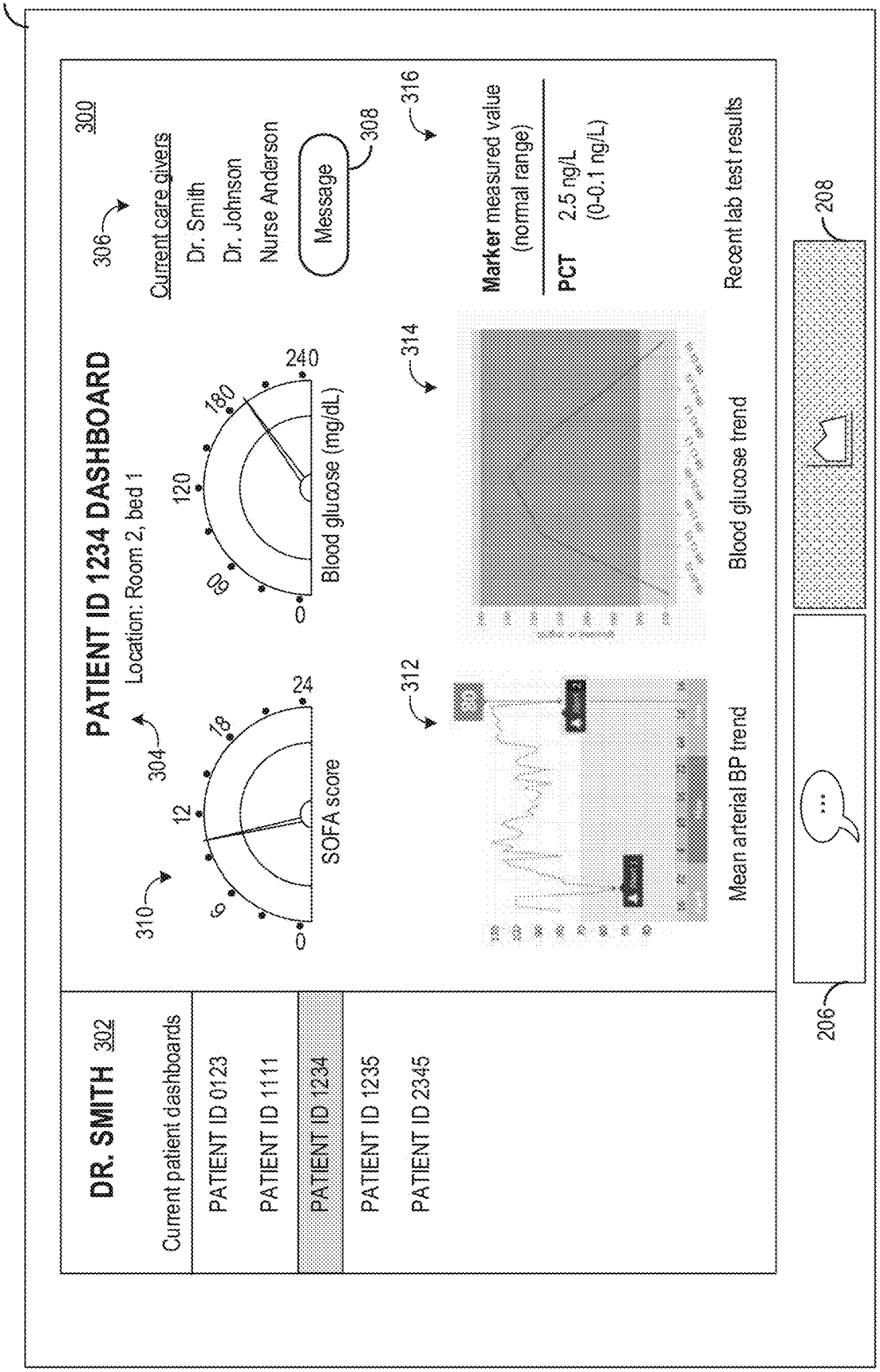
FIG. 3 shows an example display device displaying a dashboard of the collaborative healthcare system.
Figure 4:
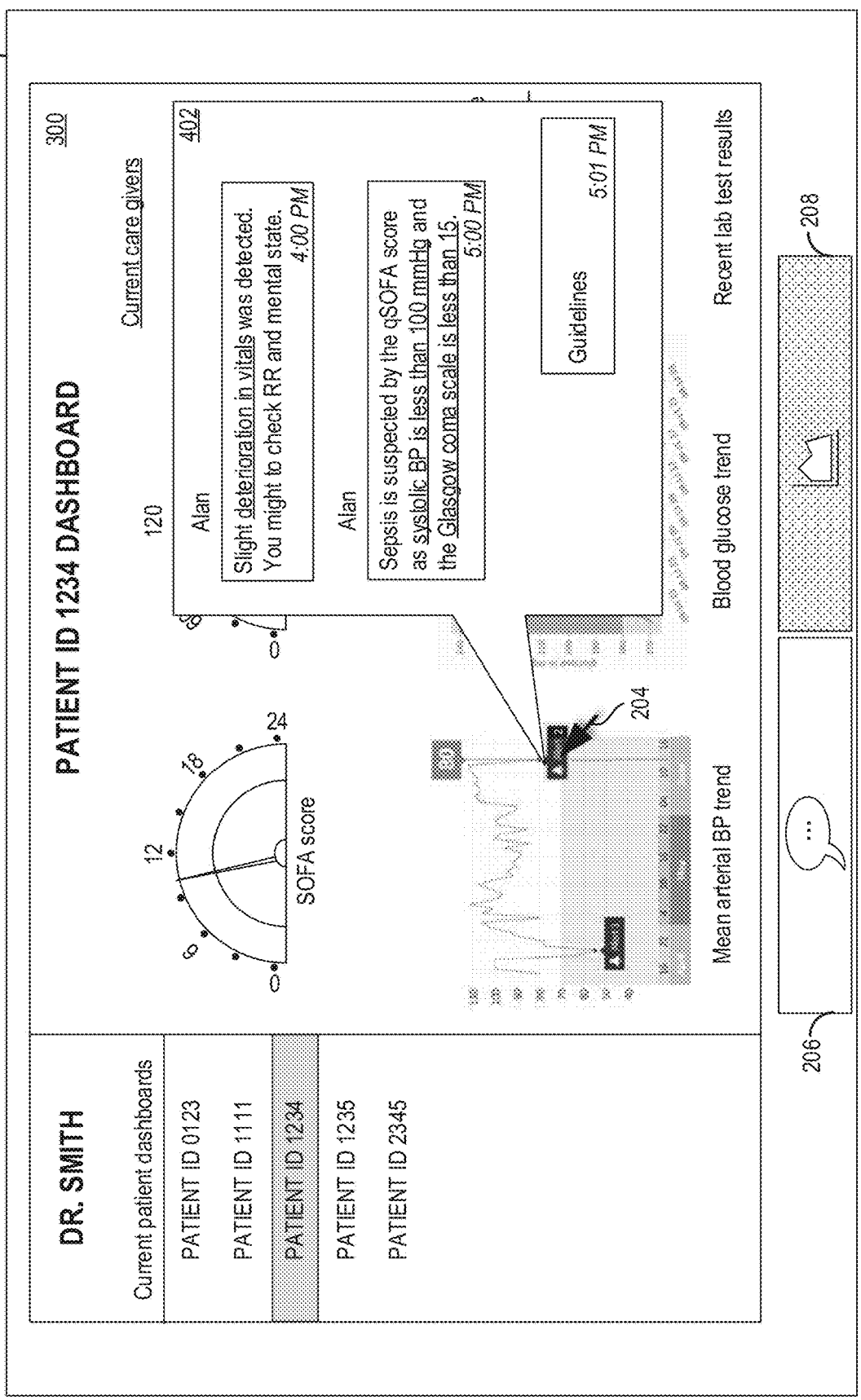
FIG. 4 shows an example display device displaying the dashboard of FIG. 3 including display of a portion of the communication thread of FIG. 2.

An example collaborative healthcare system is shown in FIG. 1. The collaborative healthcare system may be included in or associated with a medical facility and may include a communication channel comprising a communication thread and a dashboard for each admitted patient of the medical facility. The collaborative healthcare system may further include one or more virtual healthcare assistants. Communication may occur on a communication channel in the form of a communication thread (e.g., of text and/or rich media messages) between care providers of the patient and the one or more virtual healthcare assistants, as shown in FIG. 2 as well as FIGS. 7-9, 13, and 14. Patient-specific medical information may be displayed to the care providers and/or other users via a dashboard. As shown in FIG. 3, the dashboard may be launched in response to a first selection of a link on the communication thread. The dashboard may be configured to display alerts output by the one or more virtual healthcare assistants, and the alerts may be selectable to launch a portion of the communication thread occurring on the communication channel, as shown in FIG. 4, or a full version of the communication thread. Additionally, a preview of the dashboard may be launched in response to a second selection of a link on the communication thread.

Figure 5:
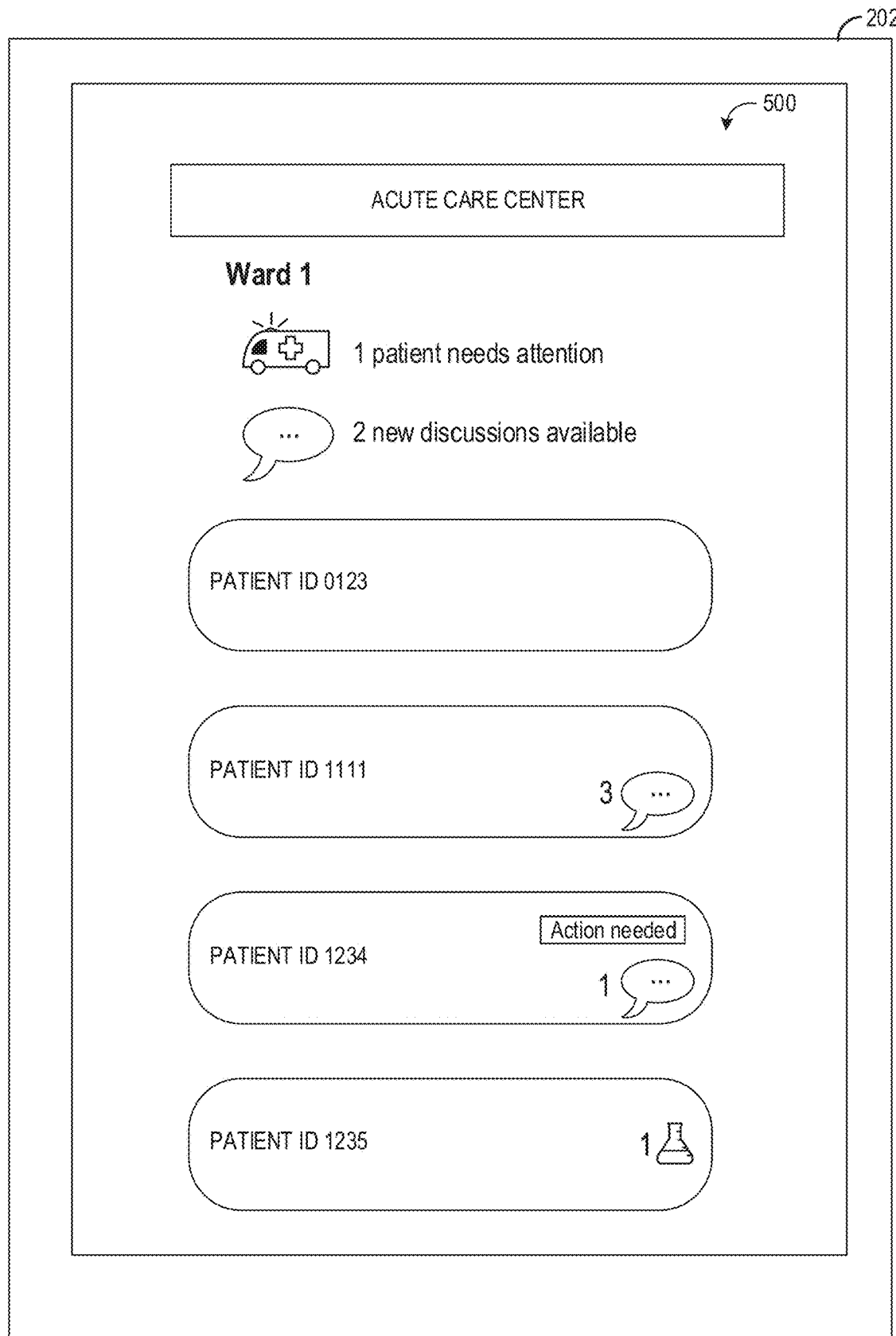
FIG. 5 shows an example display device displaying a collaborative interface.
Figure 6:
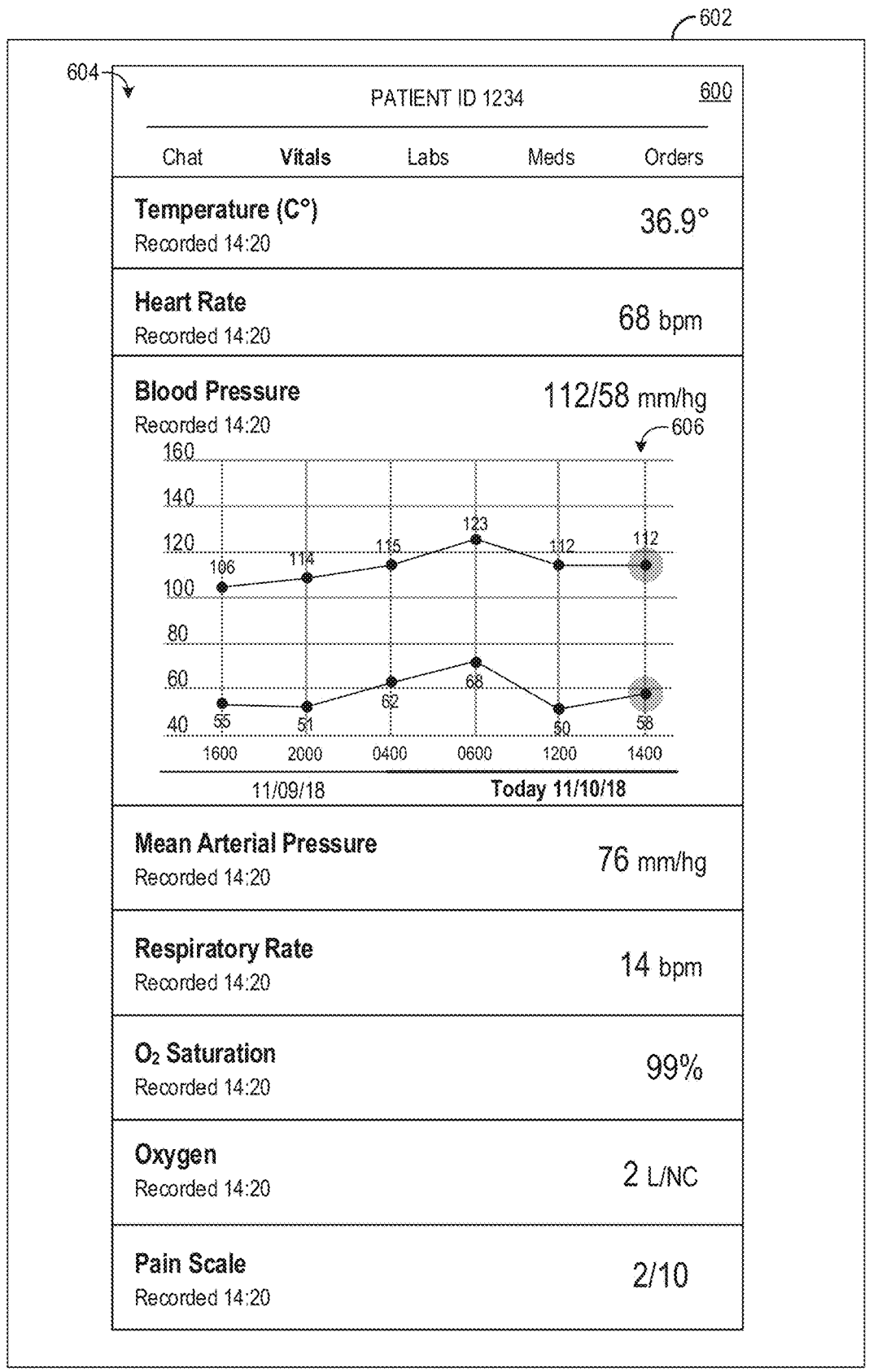
FIG. 6 shows an example display device displaying another example dashboard of the collaborative healthcare system.

Further, a collaborative system interface, as shown in FIG. 5, may be displayed on a suitable display device in order to allow a user to select a communication channel or dashboard to view. In some examples, the dashboard may take on a different visual form, as shown in FIG. 6, and a user may navigate between the dashboard and communication thread using a menu that also allows the user to access additional information pertaining to the patient (e.g., medications, lab tests, etc.), as shown in FIG. 6 as well FIGS. 7-9, 13, and 14.

Figure 10:
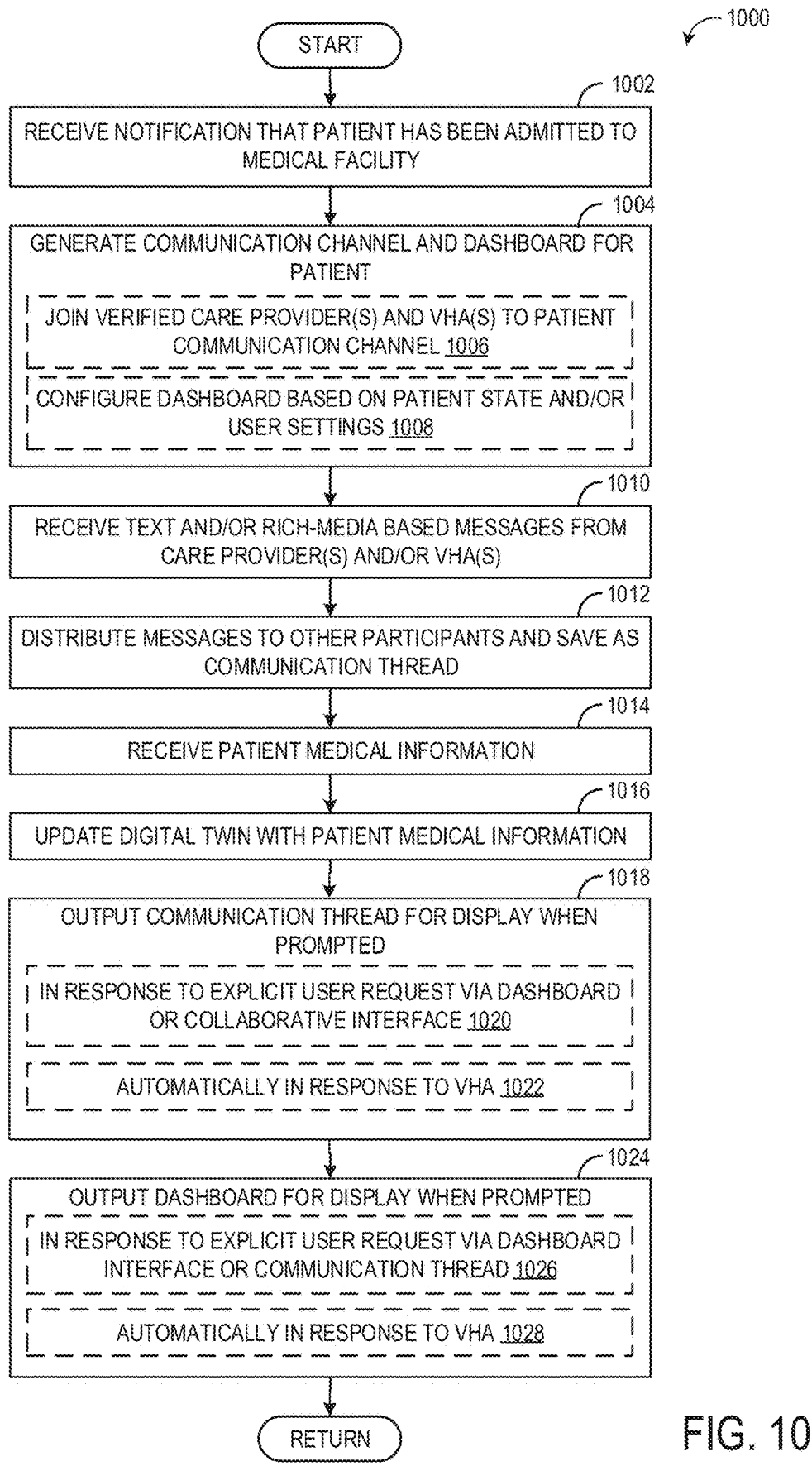
FIG. 10 is a flow chart illustrating an example method for facilitating communication within a collaborative healthcare system.
Figure 11:
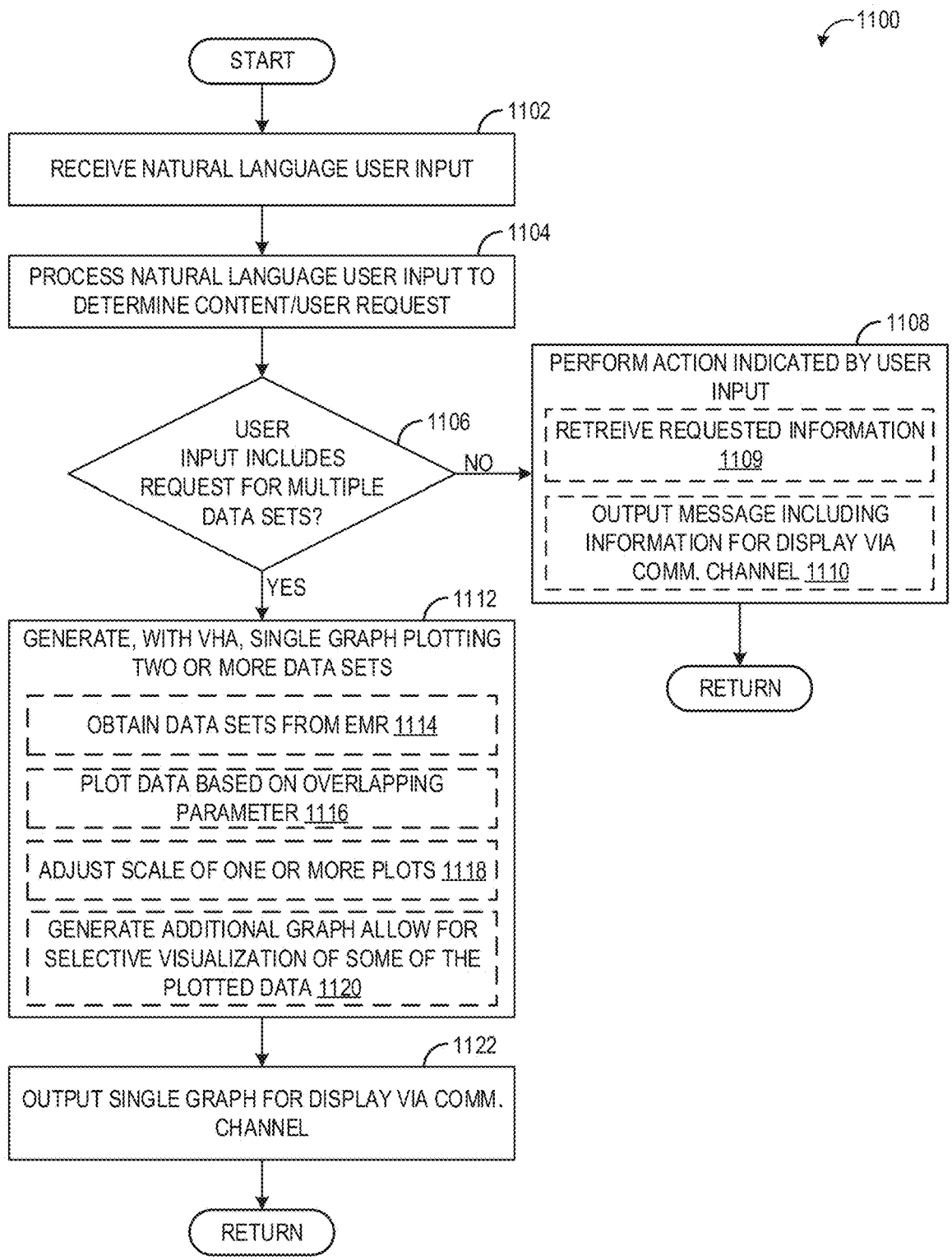
FIGS. 11 and 12 are flow charts illustrating example methods for one or more virtual healthcare assistants of the collaborative healthcare system.
Figure 12:
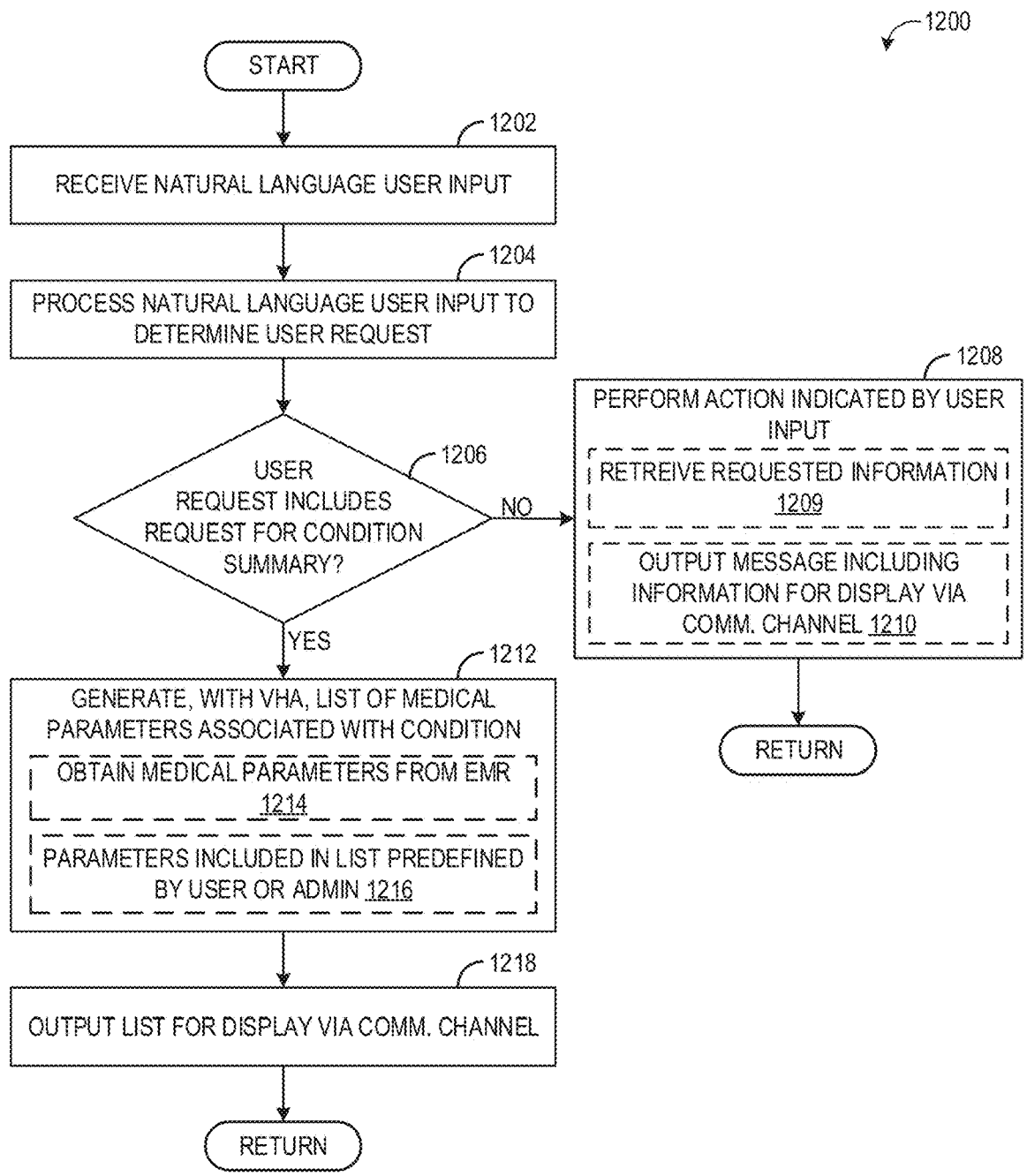

The communication thread-dashboard pairs may be generated and accessed according to the method illustrated in FIG. 10. The virtual healthcare assistants may provide assistance to the care providers of the patient by retrieving medical information of the patient from an electronic medical record and generating aggregate views of the medical information. For example, as shown by the method of FIG. 11, multiple plots of different medical data sets may be included in a single graph and output for display in response to a single request from a care provider or other user. In another example, as shown by the method of FIG. 12, a list of patient medical parameters associated with a patient medical condition may be assembled and output for display in response to a single request from a care provider or other user.

FIG. 1 schematically shows an example collaborative healthcare system 100 that may be implemented in medical facility such as a hospital. Collaborative healthcare system 100 may include a collaborative space server system 102. Server system 102 may include resources (e.g., memory 130, processor(s) 132) that may be allocated to store and execute a communication thread, a dashboard, and a digital twin for each of a plurality of patients. For example, as shown in FIG. 1, a communication thread 104, dashboard 106, and digital twin 108 are stored on server system 102 for a first patient (patient 1); a plurality of additional communication threads, dashboards, and digital twins may be stored on server system 102, each corresponding to a respective patient (patient 2 up to patient N).

As explained above, the communication thread 104 may facilitate communication among a care provider team (which may include multiple care providers that are each providing care to the patient (e.g., patient 1)) as well as one or more virtual healthcare assistants (explained in more detail below). Messages sent on the communication thread 104 may be saved and may be accessible via the dashboard 106 (and the dashboard may be accessible via the communication thread). Further, the patient medical information, including medical history, current state, vital signs, and other information, may be entered to the digital twin 108, which may be used to gain situational awareness, clinical context, and medical history of the patient to facilitate predicted patient states, procurement of relevant treatment guidelines, patient state diagnoses, etc.

Communication occurring on communication thread 104 may be displayed on one or more suitable display devices associated with a respective care provider device and/or medical facility administration device. Likewise, dashboard 106 may be displayed on the one or more display devices. As shown in FIG. 1, a plurality of care provider devices, from a first care provider device 134, a second care provider device 136, and on up to an nth care provider device 138, may be communicatively coupled to server system 102. Each care provider device may include a processor, memory, communication module, user input device, display (e.g., screen or monitor), and/or other subsystems and may be in the form of a desktop computing device, a laptop computing device, a tablet, a smart phone, or other device. Each care provider device may be adapted to send and receive encrypted data and display medical information, including medical images in a suitable format such as digital imaging and communications in medicine (DICOM) or other standards. The care provider devices may be located locally at the medical facility (such as in a nurses station or in the room of a patient) and/or remotely from the medical facility (such as a care provider's mobile device).

When viewing communication thread 104 and/or dashboard 106 via a display of a care provider device, a care provider may enter input (e.g., via the user input device, which may include a keyboard, mouse, microphone, touch screen, stylus, or other device) that may be processed by the care provider device and sent to the server system 102. In examples where the user input is a message to be sent to other care providers and/or one or more virtual healthcare assistants, the message may be sent to the server system 102, where the message may be saved as part of the communication thread 104 and then the server system 102 may send the message to other verified participants on the communication channel (e.g., the other care providers and/or one or more virtual healthcare assistants that are joined to the communication channel). In examples where the user input is a selection of a link or user interface control button of the dashboard, the user input may trigger display of the communication thread, trigger progression to a desired state of the dashboard (e.g., trigger display of desired patient medical information), trigger updates to the configuration of the dashboard, or other actions.

The collaborative space server system 102 may be communicatively coupled to hospital operational systems 118. The hospital operational systems 118 may store and/or control a variety of hospital-, care provider-, and patient-related information, including but not limited to patient admission information (including date of admission and location of the patient within the medical facility), patient care protocols and workflows, and care provider information including which care providers are monitoring/treating which patients. Further, the hospital operational systems 118 may be communicatively coupled to a plurality of monitoring devices 120, an electronic medical records (EMR) database 122 (described in more detail below), and one or more of the care provider devices. The monitoring devices 120 may include traditional medical devices monitoring respective patients, such as pulse oximeters, heart rate monitors, blood glucose monitors, and ECGs, as well as microphones, cameras, and other devices. The monitoring devices 120 may send output directly to the server system 102 and/or may send output to the hospital operational systems 118, EMR database 122, and/or one or more care provider devices. For example, a plurality of monitoring devices monitoring patient 1 may be configured to send output to the server system 102 and the server system 102 may be configured to send some or all of the data output by the monitoring devices to a care provider device (such as care provider device 134). Further, in some examples, server system 102, hospital operational systems 118, and/or EMR database 122 may receive diagnostic imaging information obtained from one or more imaging modalities, such as ultrasound, CAT, MM, X-ray, etc.

The hospital operational systems 118 may direct creation of and control access to each communication thread and dashboard. For example, when a patient is admitted, the hospital operational systems 118 may associate the patient with an identifier (e.g., an identification code) and notify the collaborative space server system 102 to generate a communication channel for that patient. When a care provider is assigned to assist in management/treatment of the patient, the hospital operational systems 118 may notify the collaborative space server system 102 to join that care provider to the patient's communication channel (the care provider may also be associated with an identifier which may be used to identify the care provider and appropriately distribute messages sent and received on the channel). In this way, the hospital operational systems 118 may control who has access to patient information. In some examples, hospital operational systems 118 and/or server system 102 may control levels of accessibility to patient information depending on the location of a care provider device (e.g., devices located at the medical facility may have access to more patient information than devices located remotely from the medical facility). Additional information about the hospital operational systems 118 is presented below.

Collaborative space server system 102 may further store instructions for (e.g., in memory 130) and be configured to execute (e.g., via processor(s) 132) a plurality of virtual healthcare assistants (VHAs). As shown, collaborative space server system 102 includes an electronic medical record (EMR) VHA 110, a guideline VHA 112, a predictive VHA 114, a listening VHA 116, and a monitoring VHA 117. The VHAs may be realized as several VHAs each for a different purpose, as described herein, various groups of VHAs (e.g., a the guideline VHA 112 and predictive VHA 114 may be combined into one VHA that is configured to both diagnose or predict patient state and output relevant guidelines), or as one overall VHA, which represents all the different attributes that will be hereby elaborated. All activations of VHAs by human care providers may be performed by using natural language including medical language, either by text or by voice.

EMR VHA 110 is configured to retrieve patient information from an electronic medical record database, such as EMR database 122, and present the retrieved data via the communication thread and/or dashboard. For example, a care provider may send a request to the EMR VHA 110, through the communication channel, for a particular piece of patient medical history saved in an EMR of the patient. The EMR VHA 110 may receive the request and determine, from the natural language of the text, that the piece of patient medical history has been requested. The EMR VHA 110 may obtain the piece of medical history from EMR database 122. The EMR VHA 110 may then send the piece of medical history to the care provider in the form of a message on the communication thread 104. In some examples where the requested piece of medical history is also saved in the digital twin 108, EMR VHA 110 may be configured to retrieve the medical history from the digital twin 108.

EMR database 122 may be an external database accessible by EMR VHA 110 via a secured hospital interface, or EMR database 122 may be a local database (e.g., housed on a device of the hospital). EMR database 122 may be a database stored in a mass storage device configured to communicate with secure channels (e.g., HTTPS and TLS), and store data in encrypted form. Further, the EMR mass storage device is configured to control access to patient electronic medical records such that only authorized healthcare providers may edit and access the electronic medical records. An EMR for a patient may include patient demographic information, family medical history, past medical history, lifestyle information, preexisting medical conditions, current medications, allergies, surgical history, past medical screenings and procedures, past hospitalizations and visits, etc.

Thus, the EMR VHA 110 serves as a connection to the EMR database. The EMR VHA may interpret questions by the human care providers regarding the patient and allows querying of the EMR database for relevant information regarding the patient (e.g. "what was the average systolic blood pressure in the last four hours?" or "show me the trend of the O2 saturation"). Queries can implicitly relate to the patient's status or medical history. The EMR VHA 110 also allows EMR-generated alerts to be formatted and sent into the patient communication thread (in a configurable manner either by a "setting" option or by voice command, such as telling it, e.g., "don't show me this again"). The EMR VHA 110 may also serve as a drug safety alerting system (including allergies, drug-to-drug relations, etc.) and may be thus connected to a relevant medical knowledgebase.

Guideline VHA 112 is configured to retrieve relevant care guidelines from an external guideline service 124. Guideline VHA 112 may be prompted, via communication occurring on communication channel, to retrieve care guidelines. For example, a care provider may explicitly request care guidelines for a given condition, such as sepsis, on the communication thread and guideline VHA 112 may query external guideline service 124 in response to the explicit request. In other examples, guideline VHA 112 may determine implicitly that care guidelines for a given patient condition are being requested and/or may be helpful. For example, guideline VHA 112 may parse communication on the communication thread 104 (e.g., between one or more care providers and/or a suitable VHA) to determine that guidelines are being requested (e.g., rather than receiving an explicit request for the guidelines, guideline VHA 112 may determine that two care providers are discussing guidelines and may retrieve the guidelines without being requested to do so). In a further example, guideline VHA 112 may determine, from patient vital signs (e.g., output by the one or more monitoring devices 120), digital twin 108, and/or other sources that a patient may be undergoing a given condition (e.g., high heart rate) and may automatically obtain guidelines for treating the condition.

External guideline service 124 may be a remote service accessed via a network, or external guideline service 124 may be a local service executed on a computing device of the hospital. The care guidelines obtained from external guideline service 124 may be preconfigured by protocols and guidelines that are specific to the medical facility that the collaborative space server system 102 services. Further, external guideline service 124 may include differential diagnoses trees that guideline VHA 112 may access to determine potential diagnoses based on a patient condition or state.

For example, with regards to the patient's state and medical history as search terms, e.g., if a diabetic patient has a high sequential organ failure assessment (SOFA) score and high glucose levels, specific guidelines will be queried without additional query terms, or alternatively the external guideline service may be queried by specifying specific guidelines. In other words, the guideline VHA may enter specific search terms to the guideline service based on patient state and symptoms (e.g., diabetes, SOFA score of five, glucose level of 190 mg/dL) to obtain one or more potential diagnoses and/or guidelines, or the guideline VHA may specifically ask for guidelines for a given condition (e.g., sepsis). The guideline VHA may also serve as a source for generating reminders for treatments that are part of a care protocol or to keep track of what decision-driving tests have been completed and what are still needed to complete the protocol. A change in patient status may be a trigger for automatic notification of relevant guidelines. The guideline VHA may also be used to plan a trajectory for the patient, of both disease progression and a care path. A patient trajectory may be determined based on the combined trajectories of vital signs, laboratory test results, or other data for that specific patient. In defining a patient trajectory, the guideline VHA may assist care providers to adjust care pathways or to stay the course and give early warning if the patient deviates from the planned trajectory.

Predictive VHA 114 is configured to retrieve predictions of future patient states from an external prediction service 126. Predictive VHA 114 may detect and issue alerts on relevant changes in the patient's state (e.g., small but worrying changes in vital signs, changes in qSOFA score). Predictive VHA 114 may also predict future events (e.g., a prediction of sepsis being developed in the coming four hours) by connecting to external prediction service 126. Predictive VHA 114 may query external prediction service 126 with search terms indicating current and/or past patient state (e.g., blood pressure trend, glucose level trend, etc.). If prediction service 126 outputs a possible future condition, the predictive VHA 114 may send an alert into the communication thread, as text, and may provide supplemental information regarding the alert. The predictive VHA 114 may also track the response of human care providers as reflected in the communication channel or in the EMR orders registry. The predictive VHA 114 may obtain patient data from the EMR and different online monitoring devices 120 (ECG, cameras, etc.) as represented in the digital twin.

Listening VHA 116 is configured to monitor communication on the communication thread 104 as well as actual human voice communication to obtain/infer various information related to the patient. In doing so, listening VHA 116 serves as a monitor, by listening to the events in the patient's surroundings including medical staff conversations and patient input (from moaning to speech). The monitored conversations/inputs may be used to record the patient's status (for EMR/digital twin) or to infer clinician reasoning (e.g., the listening VHA may catch an order to prescribe a certain antibiotic by a doctor, and understand an infection is suspected). The listening VHA 116 may receive output from one or more microphones positioned in proximity to the patient, for example, in order to monitor the conversations and inputs.

Monitoring VHA 117 is configured to receive output from the monitoring devices 120 and may track a patient condition or state based on the received output. In some examples, monitoring VHA 117 may present the received data via the communication thread and/or dashboard. For example, a care provider may send a request to the monitoring VHA 117, through the communication channel, for a particular piece of patient monitoring data, such as current heart rate. The monitoring VHA 117 may receive the request and determine, from the natural language of the request, that the patient medical data has been requested. The monitoring VHA 117 may obtain the patient medical data from the relevant monitoring device of the monitoring devices 120. The monitoring VHA 117 may then send the medical data to the care provider in the form of a message on the communication thread 104. In some examples, monitoring VHA 117 may be configured to save the medical data at the digital twin 108. Further, medical data received by monitoring VHA 117 may be displayed via the dashboard. In some examples, monitoring VHA 117 may obtain patient medical data only in response to a request from a care provider. In other examples, additionally or alternatively, monitoring VHA 117 may obtain medical data from the monitoring devices 120 independently of care giver request, and may output requested medical data when a care giver requests the data and/or when the received medical data is detected (by the VHA) as being abnormal, having changed, or otherwise indicative of an urgent patient state. In some examples, monitoring VHA 117 may be configured to provide received medical data to predictive VHA 114 and/or guideline VHA 112 in order to predict a future patient state based on current patient medical data and/or retrieve relevant care guidelines based on current patient medical data.

The VHAs may be configured to receive messages from human care providers and utilize natural language processing to determine what information is being conveyed in the messages. For example, the VHAs may utilize natural language processing to determine if a message received on the communication channel includes a request for patient medical information, and if so, determine what medical information is being requested. The VHAs may also be configured to process medical information of the patient (e.g., vital signs, medical history, current symptoms) received from the patient EMR, the monitoring devices, the care providers, and/or other sources and determine which parameters of the medical information may be used (e.g., entered into the guideline or prediction service) to determine a patient state (such as determine the likelihood the patient is experiencing a certain condition, such as sepsis). The VHAs may execute deep learning models (e.g., machine learning or other deep learning models such as neural networking) that are trained to understand medical terminology. Further, the deep learning models may be configured to learn updates or modifications to the models in an ongoing manner in a patient and/or care provider specific manner. For example, a predictive VHA may execute a deep learning model that is trained to determine that low blood pressure may be a symptom of relevance that should be entered into a prediction service or diagnosis tree, but then may be trained for a specific patient that low blood pressure for that patient is benign and may have less relevance.

The models may be trained in a suitable manner. In a first example, the models may be rule-based assistants that are configured with a set of answers for predetermined, likely questions. When a VHA receives a question, the VHA may be configured to output an answer from the set of answers. In a second example, the models may include directed acyclic graphs (DAG) of states, each of which include rules for how to react and how to proceed to various questions. However, such VHAs may only be configured to respond when there is a clear indication of the user intent (e.g., the user presses on a button "obtain heart rate") and entities (answer to "please provide the patient's date of birth" with a date).

Thus, the VHAs described herein may include artificial intelligence and be adapted to handle natural language which is a way to take human input and map it to intent and entities. The VHAs may be adapted to hold a state and map the state with (intent, entities) to an actionable API. The mapping may be performed by teaching machine learning models by providing the models with examples of such mappings. If a VHA is autonomous, the VHA may include a prediction or other mechanism that may trigger the VHA to initiate communication. The VHAs may also be configured to vary their reactions to make the VHAs more human like (this may also be performed by providing examples to a machine learning training algorithm).

Further, the training mechanism utilized may be specific for different VHAs. For example, the listening VHA (and the natural language processing engines of the other VHAs) may execute deep networks trained for natural language with medical language. This may be combined with taxonomies from the medical domain. The EMR VHA and the guideline VHA may receive the output (intent and entities) from the listening VHA and/or the respective natural language processing engine and map the output to queries. The VHAs may be trained by having examples of the best results of existing queries. The predictive VHA may be trained on its own clinical task. For example, if the predictive VHA is to predict if a patient will survive early release from an intensive care unit, then the predictive VHA may be trained on data of patients that were in the ICU and were released at different stages.

Additional VHAs may be included on the server system, such as VHAs specific to a patient state. Such an example may include a sepsis VHA that may only be joined to a patient communication channel when that patient is undergoing or at risk of developing sepsis. The sepsis VHA may be trained to specifically predict sepsis, obtain treatment guidelines for sepsis, suggest optimal lab tests to diagnose sepsis and/or monitor sepsis progression, and/or suggest treatment options for sepsis. Other VHAs may include a patient comfort VHA (e.g., a VHA configured to detect or predict patient pain, discomfort, hunger, or other symptoms not necessarily indicative of a particular medical condition but which care providers may want to be notified of to improve patient comfort), a communication VHA (e.g., that parses communication from care givers and facilitates sharing of information among the VHAs), and/or other VHAs. Further, various configurations of VHAs not disclosed above are within the scope of this disclosure, such as related VHAs being grouped into a single VHA (e.g., the monitoring and EMR VHAs being combined as one medical data VHR). For example, a single VHA may be trained for all of the above-described VHA possible skills.

A global view of multiple or all patient communication thread-dashboard pairs may be provided via to one or more of the care provider devices and the hospital operational systems 118. For example, the choice of the specific thread/dashboard pair to access may be controlled by an access application executing on collaborative space server system 102 that allows to a user to view all the relevant patients (for example, communication thread-dashboard pairs for all the patients being treated/monitored in a nurses station may be accessed on a workstation at the nurses station, or communication thread-dashboard pairs for all the patients being treated/monitored by a given care provider may accessed by that care provider on his or her mobile device). In some examples, alerts and important events within all the relevant communication channels will be signified in the global view. The choice to go into a specific communication channel may be made by a user picking the patient in the global view (or by an explicit voice command), but may be also be automated using automatic mechanisms which may detect the position of the care provider in respect to a patient (such as via BLUETOOTH® when entering a patient's proximity or based the context of a detected discussion).

The access application may allow export of only specific widgets (such as the blood pressure graph of a patient) of a communication thread and/or dashboard, or may allow more compound parts (such as a patient dashboard or a portion of the thread) to selected external applications and/or devices. For example, as explained above, devices located off-site of the medical facility may only be allowed access to some of the patient medical data, and the access application may control which patient medical data is viewable outside of the medical facility.

A management application executed on hospital operational systems 118 and/or collaborative space server system 102 may allow an administrator to update the care team that has access to a patient's communications channel, as described above. The management application may include an interface for configuring hospital specific protocols and care guidelines. The management application may also aggregate information from the communication channels to be used to predict needs for hospital operations, presenting forecasts for capital, disposable, and human assets based on aggregate acuity or disease statistics. Moreover, analytics of the information on the communication channel may be employed to improve the system and its predictors.

Collaborative space server system 102 includes a communication module 128, memory 130, and processor(s) 132 to store and execute the communication channel-dashboard pairs, digital twins, and VHAs, as well as send and receive communications, graphical user interfaces, medical data, and other information.

Communication module 128 facilitates transmission of electronic data within and/or among one or more systems. Communication via communication module 128 can be implemented using one or more protocols. In some examples, communication via communication module 128 occurs according to one or more standards (e.g., Digital Imaging and Communications in Medicine (DICOM), Health Level Seven (HL7), ANSI X12N, etc.). Communication module 128 can be a wired interface (e.g., a data bus, a Universal Serial Bus (USB) connection, etc.) and/or a wireless interface (e.g., radio frequency, infrared, near field communication (NFC), etc.). For example, communication module 128 may communicate via wired local area network (LAN), wireless LAN, wide area network (WAN), etc. using any past, present, or future communication protocol (e.g., BLUETOOTH™, USB 2.0, USB 3.0, etc.).

Memory 130 one or more data storage structures, such as optical memory devices, magnetic memory devices, or solid-state memory devices, for storing programs and routines executed by processor(s) 132 to carry out various functionalities disclosed herein. Memory 130 may include any desired type of volatile and/or non-volatile memory such as, for example, static random access memory (SRAM), dynamic random access memory (DRAM), flash memory, read-only memory (ROM), etc. Processor(s) 132 may be any suitable processor, processing unit, or microprocessor, for example. Processor(s) 132 may be a multi-processor system, and, thus, may include one or more additional processors that are identical or similar to each other and that are communicatively coupled via an interconnection bus.

As used herein, the terms "sensor," "system," "unit," or "module" may include a hardware and/or software system that operates to perform one or more functions. For example, a sensor, module, unit, or system may include a computer processor, controller, or other logic-based device that performs operations based on instructions stored on a tangible and non-transitory computer readable storage medium, such as a computer memory. Alternatively, a sensor, module, unit, or system may include a hard-wired device that performs operations based on hard-wired logic of the device. Various modules or units shown in the attached figures may represent the hardware that operates based on software or hard-wired instructions, the software that directs hardware to perform the operations, or a combination thereof.

"Systems," "units," "sensors," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

One or more of the devices described herein may be implemented over a cloud or other computer network. For example, server system 102 is shown in FIG. 1 as constituting a single entity, but it is to be understood that server system 102 may be distributed across multiple devices, such as across multiple servers.

While not specifically shown in FIG. 1, additional devices described herein (care provider device 134, care provider device 136, and care provider device 138, hospital operational systems 118, monitoring devices 120, EMR database 122, external guideline service 124, external prediction service 126) may likewise include user input devices, memory, processors, and communication modules/interfaces similar to communication module 128, memory 130, and processor(s) 132 described above, and thus the description of communication module 128, memory 130, and processor(s) 132 likewise applies to the other devices described herein. As an example, the care provider devices (e.g., care provider device 134) may store user interface templates in memory that include placeholders for relevant information stored on server system 102. For example, care provider device 134 may store a user interface template for a patient dashboard that a user of care provider device 134 may configure with placeholders for desired patient information. When the dashboard is displayed on the care provider device, the relevant patient information may be retrieved from server system 102 and inserted in the placeholders. The patient information may include current patient vital signs, VHA alerts, desired patient state trends, or other information, as explained in more detail below. The user input devices may include keyboards, mice, touch screens, microphones, or other suitable devices.

FIG. 2 shows an example communication thread 200 of a patient-specific communication channel, and as such may be a non-limiting example of communication thread 104. Communication thread 200 may be displayed on a display device 202. Display device 202 may include a screen on which the communication thread is displayed and may be coupled to and/or included as a part of a computing device, such as care provider device 134. Communication thread 200 may be displayed in response to a user request to display the communication thread. For example, the user (e.g., a care provider) may access a collaborative system interface that includes a global view of all communication threads and dashboards the user is authenticated to participate in (which may include all patients at the medical facility the care provider is attending to) and may select a desired communication thread to view. An example collaborative system interface 500 is shown in FIG. 5. Collaborative system interface 500 may be displayed on display device 202 or other suitable device and may include all patients admitted to a specific unit or ward of a medical facility. As shown, collaborative system interface 500 includes identifying information specifying the medical facility ("acute care center") and relevant unit ("ward 1") of the medical facility, and further includes links to patient-specific communication threads and dashboards for the patients in that unit of that medical facility. However, in other examples, the patients shown via collaborative system interface 500 may specific to a certain care provider.

Collaborative system interface 500 may include a notification section whereby the user viewing collaborative system interface 500 may be notified of urgent patient conditions, active communication channel discussions, lab test results, and other information. For example, collaborative system interface 500 includes a notification section that shows that one patient requires attention (e.g., due to deteriorating vital signs) while two new discussions are available.

Collaborative system interface 500 further includes links to patient communication thread-dashboard pairs. For example, FIG. 5 shows links to communication thread-dashboard pairs for patient ID 0123, patient ID 1111, patient ID 1234, and patient ID 1235. As explained above, each patient may be assigned an identifier that may be used to identify the patient on the communication thread and dashboard. In other examples, other mechanisms for identifying the patient may be used, such as location (e.g., bed 2 in room 4) and/or actual patient name. Additional patient links may be viewed by scrolling the interface. Each patient link may include notifications where relevant. For example, the link for patient ID 1111 includes a notification that three new messages are available to be viewed on the communication channel for that patient. The link for patient ID 1234 includes a notification that action is needed (e.g., due to high blood pressure or other significant vital sign being detected, which will be explained in more detail below) as well as a notification that one new message is available on the communication channel for that patient. In some examples, when a lab test result for a patient is available, the link for that patient may include a notification of an available lab test result, such as the notification displayed in the link for patient ID 1235. In examples, care providers may be notified of available lab test results through the communication channel for the patient, and thus the notification may include a notification that a new message is available.

Selection of a patient link may launch the communication thread or dashboard for that patient. For example, selection of the link for patient ID 1234 may launch the communication thread 200 for patient ID 1234, shown FIG. 2 and explained in more detail below.

Returning to FIG. 2, communication thread 200 may include an identification header 204 that identifies the patient being discussed/monitored via the communication thread. In the illustrated example, communication thread 200 is specific to patient ID 1234. In the illustrated portion of communication thread 200, communication is occurring between a care provider (e.g., Dr. Smith) and a virtual healthcare assistant that, in the illustrated example, has a human persona and as such includes a human name (Alan). Communication thread 200 is being viewed by Dr. Smith, although any authenticated/approved user may view communication thread 200. As shown by the first message from the top, Dr. Smith is requesting medical information relating to the patient from the VHA by asking, in natural language, for a heart rate graph ("Could I get the HR graph please"). In response, the VHA sends an image of the patient's heart rate graph, which may be obtained or assembled from the patient's EMR data. The image of the heart rate graph is viewable in the communication thread and may also be selected via suitable user input to view in a different form, such as via the patient dashboard.

At a later time (e.g., 4:00 PM), the VHA outputs an alert/notification in the communication thread indicating a change in patient status, herein a deterioration in vitals. The alert is accompanied by a suggested course of action that a care provider may take, including checking respiratory rate and mental state. The VHA issues another alert at 5:00 PM indicating that sepsis is suspected based on a quick SOFA score (qSOFA), owing to low systolic blood pressure and a low Glasgow coma scale. The alerts issued by the VHA may include links to the patient dashboard, for example, allowing a user to select a link to launch the dashboard and view the medical data relating to the alerts. For example, the alert "systolic BP is less than 100 mmHg" is shown in underline, indicating a link to additional information is available. A user may select the link via a suitable input, such as via a mouse click, touch input, or voice command. In some examples, selecting a link with a first selection (e.g., a double click) may launch the patient dashboard (as shown in FIG. 3). Selecting a link with a second selection (e.g., a single click or a hover) may launch a preview where only the patient's blood pressure graph is shown.

In response to the alert regarding the potential sepsis, Dr. Smith asks for guidelines at 5:01 PM. Because the VHA had immediately previously issued the alert regarding the possible sepsis due to the qSOFA score, the VHA may assume that the guidelines being requested by Dr. Smith include guidelines for sepsis based on a qSOFA score. In response, the VHA retrieves guidelines from an external guideline service relating to qSOFA scores and outputs the guidelines into the communication thread. As shown, only a portion of the guidelines are displayed in the communication thread. By selecting the link (the underlined "qSofa guidelines"), the user may be taken to a different interface where the full guidelines are displayed, or the full guidelines may be displayed over the top of the still-displayed communication thread.

While not shown in FIG. 2, communication thread 200 may include a search box/functionality where a user may search for past messages on the communication thread. For example, a user may enter a command (by voice or text) requesting that all messages related to the patient's heart rate be displayed. Also displayed on display device 202 is a communication thread button 206 and a dashboard button 208. In FIG. 2, the user is viewing the communication thread 200 occurring on the communication channel. Hence, the communication thread button 206 is highlighted. To switch to the dashboard for patient ID 1234, the user may select the dashboard button 208. Additionally or alternatively, the user may request to view a vital signs interface by selecting a link within the identification header 204 (e.g., by selecting "vitals"). The vital signs interface, which is discussed in more detail below with respect to FIG. 6, may serve as an additional or alternative dashboard, wherein additional medical information of the patient may be displayed. The user may request to view additional interfaces via the identification header 204, such as a labs interface, where lab results may be displayed, a meds interface, where medicine dosage, timing, and other information may be displayed, and an orders interface, where testing orders (such as diagnostic imaging tests, lab tests, or other tests) may be displayed.

As explained above, FIG. 2 shows communication between a care provider and a virtual healthcare assistant ("Alan"), where Alan provides all the information requested by the care provider as well as provides alerts/notifications. In this way, Alan is performing the functions described above with respect to FIG. 1 ascribed to the predictive VHA, EMR VHA, and guidelines VHA. It is to be understood that in some examples, each of the different VHAs may interact with the communication thread individually.

FIG. 3 shows an example dashboard 300 that may be displayed on display device 202 or other suitable device. Dashboard 300 may be displayed in response to a user input to the communication thread 200, for example by selecting a link within medical information displayed in communication thread, as explained above, or in response to selection of the dashboard button 208. However, dashboard 300 may be displayed in response to other inputs, such as in response to a user input selecting the dashboard from the collaborative system interface of FIG. 10 that includes a global view of multiple communication threads and dashboards. Additionally, FIG. 3 shows a side bar 302 displayed along with dashboard 300 showing patient dashboards for the patients Dr. Smith is currently attending. User input to the side bar may launch a different dashboard, for example Dr. Smith may select to view each of the currently available dashboards to quickly assess the status of each patient.

Dashboard 300 may be configured to display patient medical information based on the current patient state and user-configured settings. For example, a dashboard for a patient that is being treated at the medical facility for pneumonia may be configured to display different medical information than a dashboard for a patient that is being treated at the medical facility for a stroke. In some examples, when a patient is admitted at the medical facility, a dashboard may be generated automatically for the patient based on the reason of admittance (e.g., pneumonia), thereby including the most relevant patient medical information for the patient's condition, such as blood oxygen level and respiration rate. A user may also configure which medical data to view via the dashboard, for example a doctor attending to the patient may choose to view heart rate rather than respiration rate.

The medical information that is displayed on the dashboard may be obtained from one or more monitoring devices currently monitoring the patient, such that the medical information is displayed on the dashboard in a real-time (or near real-time) manner. Additionally or alternatively, the medical information that is displayed on the dashboard may be obtained from the patient's EMR, the digital twin associated with the patient, and/or the communication thread. As explained above, one or more VHAs may obtain patient medical information from the patient's EMR, the monitoring devices, guideline services, or other sources and include the obtained medical information as a message in a communication thread on the communication channel. To view the medical information in greater detail, the user may select the medical information from the communication thread, where the medical information may then be displayed in the dashboard.

Additional information may also be displayed via the dashboard, such as patient information (location, demographics, medical history), care provider information (such as which doctors, nurses, and/or other care providers are attending to the patient), and a timeline of selected or relevant messages from the communication thread. For example, the most recent alerts may be displayed as a timeline on the dashboard.

Referring to dashboard 300 as an example, patient information 304 is displayed at the top of the dashboard, including patient identification and location. Care provider information 306 is also displayed in dashboard 300, including current care providers for the patient. Additionally, a user interface control button 308 is shown that, when selected, may allow the care provider viewing dashboard 300 to view and interact with the communication thread.

Dashboard 300 further includes real-time medical information indicators 310. As shown, the indicators 310 include a SOFA score and blood glucose level, depicted as gauge charts with respective needles that move to indicate current SOFA score and blood glucose relative to a range of possible SOFA scores and blood glucose levels. While not shown in FIG. 3, the gauge charts may include color coding for quick determination of normal, intermediate, and high scores/ levels, for example. The gauge charts shown are exemplary in nature and patient medical information may be shown in other forms.

Dashboard further includes medical history trends, including a first graph 312 depicting mean arterial blood pressure trend (e.g., blood pressure as a function of time) and a second graph 314 depicting blood glucose trend (e.g., blood pressure as a function of time). The medical history trends shown in FIG. 3 may be displayed on the dashboard in response to a request from a user (e.g., in response to a care provider selecting a link to patient medical history from a communication thread), due to a preconfigured dashboard setting, or other suitable trigger. For example, as shown in FIG. 2, the VHA issued an alert at 5:00 PM that included reference to patient blood pressure in the form of a link. When the link is selected (e.g., via cursor 204), the dashboard 300 may be displayed showing the first graph 312 of the patient's blood pressure trend.

Dashboard 300 further includes a recent lab test results section 316, where the results from recent lab tests may be displayed. For example, the user may have selected a link to available procalcitonin (PCT) test results displayed as part of a communication thread, which may result in display of dashboard 300. Via the recent lab test results section 316, the user (care provider) may be notified that the PCT test for that patient is relatively high and thus sepsis is confirmed or suspected.

As explained earlier, one or more of the virtual healthcare assistants may be configured to monitor patient vital signs, via the output from the monitoring devices, the information stored in the digital twin, or other source. If a vital sign (or other health parameter) meets a predetermined condition, the one or more virtual healthcare assistants may be configured to output an alert to notify the one or more care providers attending the patient that patient follow-up may be needed. The alerts may be included in the communication thread, as discussed above. Additionally or alternatively, the alerts may be displayed on the dashboard. As shown, first graph 312 includes two alerts, each alert issued when mean arterial blood pressure dropped below a threshold, such as 80 mmHg, or trended in an unexpected way, such as five consecutively decreasing values which may or may not be below the 80 mmHg threshold. Selection of an alert may trigger display of a portion of the communication thread occurring on the communication channel where the alert was referenced.

Thus, as shown in FIG. 4, in response to user input selecting the second alert displayed on the dashboard 300 (e.g., the "alert 2" box) via cursor 204, a portion 402 of the communication thread 200 shown in FIG. 2 is displayed over dashboard 300. The portion 402 displayed may include only the portion of the communication thread that references the medical information that triggered the alert, and may also include additional messages around the message referencing the alert, in order to place the alert in context. In this way, a user may be able to quickly determine what else may have occurred around the time the alert was issued, determine if attending care providers administered treatment, or determine other relevant information. The portion 402 may not include the most recent messages in the communication thread, in some examples. Further, a user may not have access to the full communication thread when viewing the portion, and may not be able to interact (e.g., send messages) with the communication channel. Thus, a different selection on the dashboard may enable a user to view the full communication thread.

Additionally or alternatively, when viewing the portion of the communication thread, the user may scroll to view other portions of the communication thread or may enter another input to the portion of the communication thread to enable viewing of the full version of the communication thread. Alternatively, instead of showing a snippet from the communication channel, the full version of the communication thread may be displayed, with the focus point being the point in the communication channel that references the alert (which may enable the user to look before and after that point of the thread if desired). In another example, only the snippet of the communication thread may be displayed and if the snippet is selected, the full version of the communication thread may be displayed. In this way, either automatically or upon a further user input, the use may be able to interact with the communication thread (e.g., send a message via the communication thread).

Thus, the collaborative healthcare system shown in FIG. 1 may generate communication channel-dashboard pairs for each patient associated with the collaborative healthcare system. The collaborative healthcare system may include one or more computing devices, such as the care provider device 134. The computing device may include a display screen, and the computing device may be configured to display on the screen a dashboard. The dashboard may include patient medical information, such as diagnostic lab test information (e.g., lab test results, pending lab tests that have been ordered but not yet fulfilled, status updates for pending lab tests, and so forth). The computing device may additionally be configured to display on the screen an alert related to the patient medical information. For example, as shown in FIG. 3, dashboard 300 may be displayed on a screen of a computing device (e.g., display device 202, which may be a screen of a computing device such as care provider device 134). Dashboard 300 may display patient medical information, such as the graph of the blood pressure trend of the patient (e.g., first graph 312) and recent lab results. The displayed medical information may include an alert, such as alert 2 shown on first graph 312.

The alert may be selectable to launch a communication thread between a care provider and a virtual healthcare assistant. For example, as shown in FIG. 4, selection of alert 2 launches a communication thread between a care provider (Dr. Smith) and a virtual healthcare assistant (Alan). The selection of the alert enables a portion of the communication thread that references the displayed patient medical information to be seen within the communication thread. For example, FIG. 4 shows that in response to selection of alert 2, a portion 402 of the communication thread 202 (shown in FIG. 2) is displayed. The portion 402 includes reference to patient blood pressure, which is also displayed on the patient dashboard. Further, the alert may be displayed on the dashboard (at least initially) while the communication thread is in an un-launched state. For example, the alert may be displayed on dashboard 300 without display of the communication thread, e.g., while the communication thread is un-launched. In some examples, the full communication thread may be displayed rather than just a portion, with the full communication thread focused at the portion that references the patient blood pressure. According to some embodiments, the communication thread and the dashboard may both be displayed simultaneously on the display device.

In this way, the computing device provides a specific manner of displaying a limited set of information (e.g., the portion of the communication thread that specifically references medical information displayed on the dashboard) to the user, rather than using conventional user interface methods to display a generic index/list on a computer that may require the user to step through multiple menus and/or lists of communications and alerts to find the relevant portion of communication regarding the medical information. The dashboard interface-communication thread link disclosed herein may be advantageous because it avoids a user having to scroll around and switch views multiple times to find desired data/functionality, thereby preventing drilling down through many layers to get the desired data/functionality which may be slow, complex, and difficult to learn. The disclosed dashboard interface-communication thread link may improve the efficiency of using the computing device by bringing together the portion of the communication thread most relevant to the user (as it relates to the displayed medical information) and the dashboard actually displaying the medical information, allowing the user to view the most relevant information on the communication thread without actually opening up the communication thread. The speed of a user's navigation through various views and windows may be improved because the disclosed link between the dashboard and the communication thread saves the user from navigating to the communication thread from the dashboard, opening the communication thread up, and then navigating within the communication thread to enable the portion of interest to be seen or a function of interest to be activated.

Thus, the collaborative healthcare system shown in FIG. 1 may generate communication thread-dashboard pairs for each patient associated with the collaborative healthcare system. The collaborative healthcare system may include one or more computing devices, such as the care provider device 134. The computing device may include a display screen, and the computing device may be configured to display on the screen a communication thread. The computing device may additionally be configured to display on the screen a dashboard that can be reached directly from the communication thread. For example, as shown in FIG. 2, the communication thread may include a link that when selected launches a dashboard, such as the dashboard 300 shown in FIG. 3.

The communication thread displays communication between a care provider and a virtual healthcare assistant, and the communication thread includes medical information of a patient. At least a portion of the displayed medical information is selectable to launch the dashboard and enable the selected medical information to be seen within the dashboard. For example, referring to FIG. 2, the communication thread includes a link referencing patient medical information (herein, lab test results), and selection of the link launches some or all of the dashboard. The dashboard includes display of the patient medical information included in the link (e.g., the lab test results). In an example, selection of the link may launch a full version of the dashboard, as shown in FIG. 3. In another example, selection of the link may launch only a portion of the dashboard. The communication thread may be displayed while the dashboard is in an un-launched state, at least initially. For example, FIG. 2 shows the communication thread being displayed without display of the dashboard, and thus the dashboard may be unlaunched until the link the communication thread is selected.

In this way, the computing device provides a specific manner of displaying a limited set of information (e.g., the dashboard that specifically includes medical information referenced in the communication thread) to the user, rather than using conventional user interface methods to display a generic index/list on a computer that may require the user to step through multiple menus and/or lists of communications and alerts to find the relevant medical information. The communication thread-dashboard interface link disclosed herein may be advantageous because it avoids a user having to scroll around and switch views multiple times to find desired data/functionality, thereby preventing drilling down through many layers to get the desired data/functionality which may be slow, complex, and difficult to learn. The disclosed communication thread-dashboard interface link may improve the efficiency of using the computing device by bringing together the medical information most relevant to the user (via the dashboard) and the communication thread referencing the medical information, allowing the user to view the most relevant medical information discussed on the communication thread without actually accessing an electronic medical record or separate interface where patient monitoring data may be displayed. The speed of a user's navigation through various views and windows may be improved because the disclosed link between the communication thread and dashboard saves the user from navigating to an electronic medical record database, opening the database up, and then navigating within the database to enable the medical information of interest to be seen or a function of interest to be activated.

As mentioned previously, an identification header may be displayed with the communication thread and may include patient identification information and user interface control buttons via which a user may enter input selecting to view a different interface related to that patient. As an example, the identification header may include a vitals button, and user selection of the vitals button (e.g., via a touch input) may cause a vital signs interface for that patient to be displayed. FIG. 6 shows an example of a vital signs interface 600 that may be displayed on a display device 602. Display device 602 may include a screen on which the vital signs interface is displayed and may be coupled to and/or included as a part of a computing device, such as care provider device 134 shown in FIG. 1.

Vital signs interface 600 includes an identification header 604, similar to the identification header described above with respect to FIG. 2. Vital signs interface 600 further includes a plurality of patient medical parameters. The plurality of patient medical parameters may include a plurality of vital signs measured by one or more patient monitoring devices, which may be stored in the patient's EMR and/or as part of the patient's digital twin. The plurality of vital signs may include temperature, heart rate, blood pressure, mean arterial pressure, respiratory rate, O2 saturation, and oxygen level, as shown, and/or may include additional or alternative vital signs. The plurality of patient medical parameters may further include assessed patient states, which may be ascertained by one or more care providers and entered into the patient's EMR. The assessed patient states may include pain (as shown), alertness level, cognition, appearance, etc.

For each medical parameter displayed on the vital signs interface 600, a name of the medical parameter may be displayed along with the most recently-recorded value for that parameter and the time/date at which the value was recorded. For example, the first vital sign displayed from the top of the vital signs interface includes temperature with a value of 36.9° C. recorded at 14:20. For some, or all, of the patient medical parameters displayed on the vital signs interface, user selection of that medical parameter may result in additional information being displayed, such as a trend graph for that parameter that may include some or all of the measured values for that parameter over a given duration. For example, as shown, a user has selected the blood pressure parameter, e.g., by entering a touch input to the blood pressure parameter displayed on the interface. As a result, a blood pressure trend graph 606 is displayed (e.g., the blood pressure section may expand downward to accommodate the graph, shifting all other parameters below it downward). The blood pressure trend graph 606 includes six blood pressure values measured in the past 24 hours and plotted as a function of time (as each blood pressure measurement includes systolic and diastolic pressure, two curves are shown, one for systolic and one for diastolic). User deselection of the blood pressure parameter (e.g., by selecting it again) may cause the blood pressure region to collapse back to its original size and displayed information, resulting in the blood pressure trend graph not being displayed. Similar trend graphs may displayed upon user selection of any of the displayed medical parameters.

The medical parameters that are displayed as part of the vital signs interface may be selected in a suitable manner. In one example, the user may customize which parameters are displayed on the vital signs interface, whether globally for all patients that the user interacts with or individually by patient. In other examples, an administrator (e.g., of the hospital) may determine which parameters are displayed. In still further examples, additionally or alternatively, the medical parameters included in a particular patient's vital signs interface may be based at least in part on the patient's diagnosed condition(s) and/or reason for admittance to the medical unit. For example, a vital signs interface specific to a patient that is diagnosed with pneumonia may have at least some different medical parameters than a vital signs interface specific to a patient undergoing a C-section.

The vital signs interface illustrated in FIG. 6 may be displayable in addition to the patient dashboard illustrated in FIGS. 3 and 4. In this way, both the dashboard of FIGS. 3 and 4 and the vital signs interface of FIG. 6 may be available to care givers as different interfaces for viewing select patient medical information. In other examples, the vital signs interface and the dashboard illustrated in FIGS. 3 and 4 may be alternative embodiments, e.g., the vital signs interface may be one example of how a dashboard may be configured and the dashboard of FIGS. 3 and 4 may be a different example of how a dashboard may be configured. In still other examples, the vital signs interface may be a "mobile interface" and the dashboard (such as the dashboard of FIGS. 3 and 4) may be a "standard interface," such that the dashboard may be viewed when the care provider device is a desktop computer, laptop, large format monitor, etc., while the vitals interface may be displayed when the care provider device is a mobile device, such as a smartphone or tablet, or otherwise includes limited display area.

Figure 7:
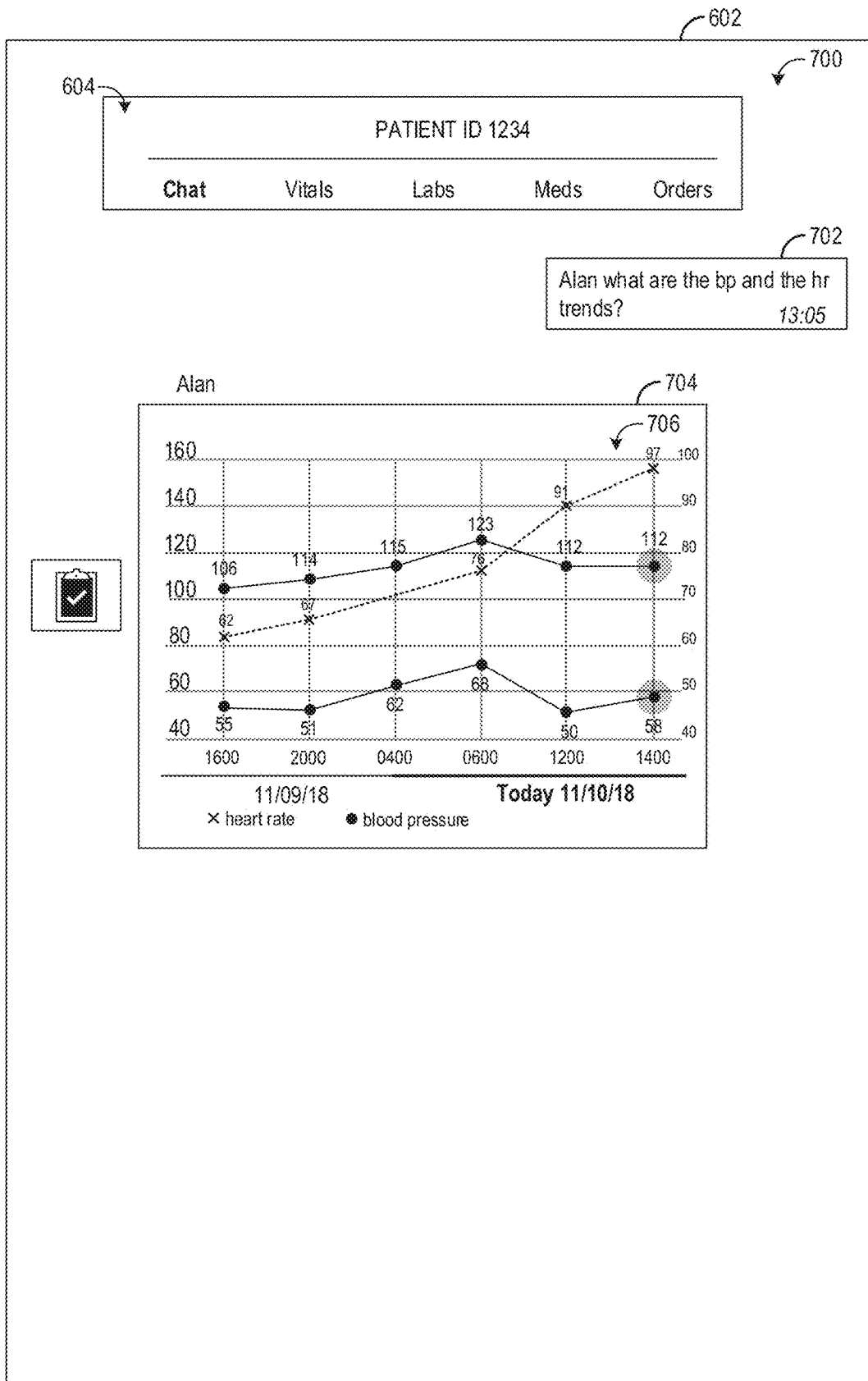
FIGS. 7-9 show an example display device displaying examples of communication threads occurring on a communication channel of the collaborative healthcare system.

FIG. 7 shows a communication thread 700 of a patient-specific communication channel, and as such may be a non-limiting example of communication thread 104 introduced in FIG. 1. Communication thread 700 may be displayed on the display device 602. Communication thread 700 may be displayed in response to a user request to display the communication thread and may include the identification header 604 that identifies the patient being discussed/monitored via the communication thread. In the illustrated example, communication thread 700 is specific to patient ID 1234. In the illustrated portion of communication thread 700, communication is occurring between a care provider (e.g., Dr. Smith) and a virtual healthcare assistant ("Alan"). Communication thread 700 is being viewed by Dr. Smith, although any authenticated/approved user may view communication thread 700.

As shown by the first message 702, Dr. Smith enters a request to view trend graphs for both blood pressure (bp) and heart rate (hr) (e.g., "Alan what are the bp and hr trends?"). The request is entered via text or voice as a natural language input, e.g., the request is conversational in nature and does not include search terms entered into search fields. The request is also directed at the virtual assistant, as the request starts with the virtual assistant's "name," Alan. The virtual assistant then processes the natural language input to determine that the natural language input includes a user request to view multiple different medical parameters. The virtual assistant then generates a single graph that includes plots of both medical parameters and outputs a message 704 into the communication thread that includes a single graph 706 plotting heart rate and blood pressure as a function of time, for the last 24 hours.

The single graph 706 includes a common x-axis (time) and a common set of gridlines, but the single graph includes two y-axes (one for heart rate values, shown in dashed line with crosses denoting measured values, and one for blood pressure values, shown in solid line with dots denoting measured values) having different units and scales. When generating the single graph, the virtual assistant may attempt to align the data being plotted based on one or more overlapping parameters (e.g., time), and may re-scale some of the data, remove some of the data (e.g., that falls outside the overlapping parameter), or otherwise automatically reconfigure how some of the data is plotted in order to increase visual clarity.

Figure 8:
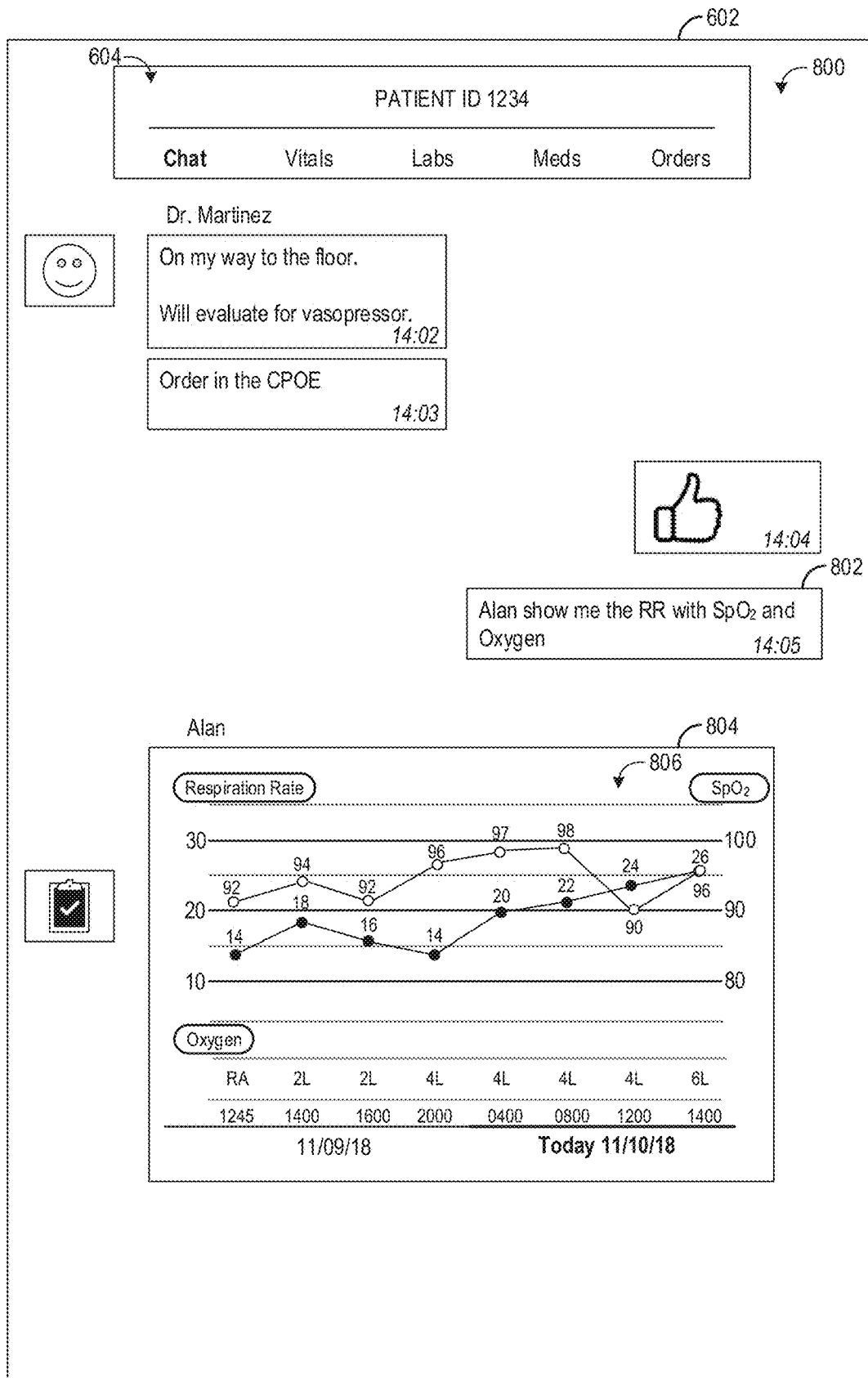

FIG. 8 shows another example communication thread 800 of a patient-specific communication channel, and as such may be a non-limiting example of communication thread 104 introduced in FIG. 1. Communication thread 800 may be displayed on the display device 602. Communication thread 800 may be displayed in response to a user request to display the communication thread and may include the identification header 604 that identifies the patient being discussed/monitored via the communication thread. In the illustrated example, communication thread 800 is specific to patient ID 1234. In the illustrated portion of communication thread 800, communication is occurring between a first care provider (e.g., Dr. Smith), a second care provider (e.g., Dr. Martinez), and the virtual healthcare assistant ("Alan"). Communication thread 800 is being viewed by Dr. Smith, although any authenticated/approved user may view communication thread 800.

Similar to communication thread 700, communication thread 800 includes a request from Dr. Smith to view multiple medical parameters, in the form of message 802. In order to clarify that the request is intended for the virtual assistant (e.g., as opposed to other care givers on the communication thread), the request is prefaced with Alan, but it should be understood that the example is non-limiting and that the virtual assistant may be able to detect and process input, and respond to the requests in the input, without explicitly being asked to do so.

The virtual assistant may process the natural language in the message (e.g., show me the respiration rate (RR) with oxygen saturation (SpO2) and oxygen flow rate) to determine that trend graphs for respiration rate, SpO2, and oxygen flow rate have been requested. The virtual assistant may obtain data sets for each requested medical parameter from the patient's EMR. For example, the virtual assistant may obtain a first data set that includes patient respiration rate over a duration (e.g., the prior 24 or 48 hours), a second data set that includes patient oxygen saturation (SpO2) over the duration, and a third data set that includes patient oxygen flow rate (e.g., a flow rate of medical oxygen provided to the patient) over the duration. The virtual assistant may then plot each data set on the same graph, in order to generate the single graph 806 that is then output as a message 804 in the communication thread.

Graph 806 includes a first plot of the first data set (e.g., respiration rate) over time, with respiration rate values on a first, left y-axis and time on the x-axis. Graph 806 further includes a second plot of the second data set (e.g., oxygen saturation values), with oxygen saturation values on a second, right y-axis and time on the x-axis. Graph 806 further includes a third plot of the third data set (e.g., the oxygen flow rate) per event, where the oxygen flow rate values are depicted as values for each event (e.g., where the events include monitoring of the oxygen flow rate, changing the oxygen tank, or other event, where the events may or may not occur at the time depicted along the x-axis), without a y-axis. By plotting the various data sets in the manner shown in FIG. 8 (e.g., with two data sets being plotted on an x-y axis and the other data set being shown as values for each event), data sets with different units and different scales of values may be accommodated on the same graph. Such an approach may be advantageous for data sets with large differences in data ranges, such as the respiration rate data set and SpO2 data sets plotted in FIG. 8, where the respiration rate data set plotted in the graph of FIG. 8 has a maximum value of 26 and a minimum value of 14, while the SpO2 data set plotted in the graph of FIG. 8 has a maximum value of 98 and a minimum value of 90. By plotting the two data sets with two different y-axes, the curves/trend lines for each plot may be brought closer together than if plotted on a single y-axis with values spanning from 10-100, for example. Further, by plotting numerical values as a function of time and "event" based information as a function of time and/or event number in a series of events, the different types of data may be presented with increased visual clarity. While FIG. 8 includes oxygen levels as an event-based parameter, the oxygen levels include numeric values (e.g., 2 liters of oxygen per minute). However, the approach described above and shown in FIG. 8 may be advantageous for parameters that do not include numeric values, such as binary states (e.g., activation/deactivation of certain medical devices, such as a heart ablation generator).

Figure 9:
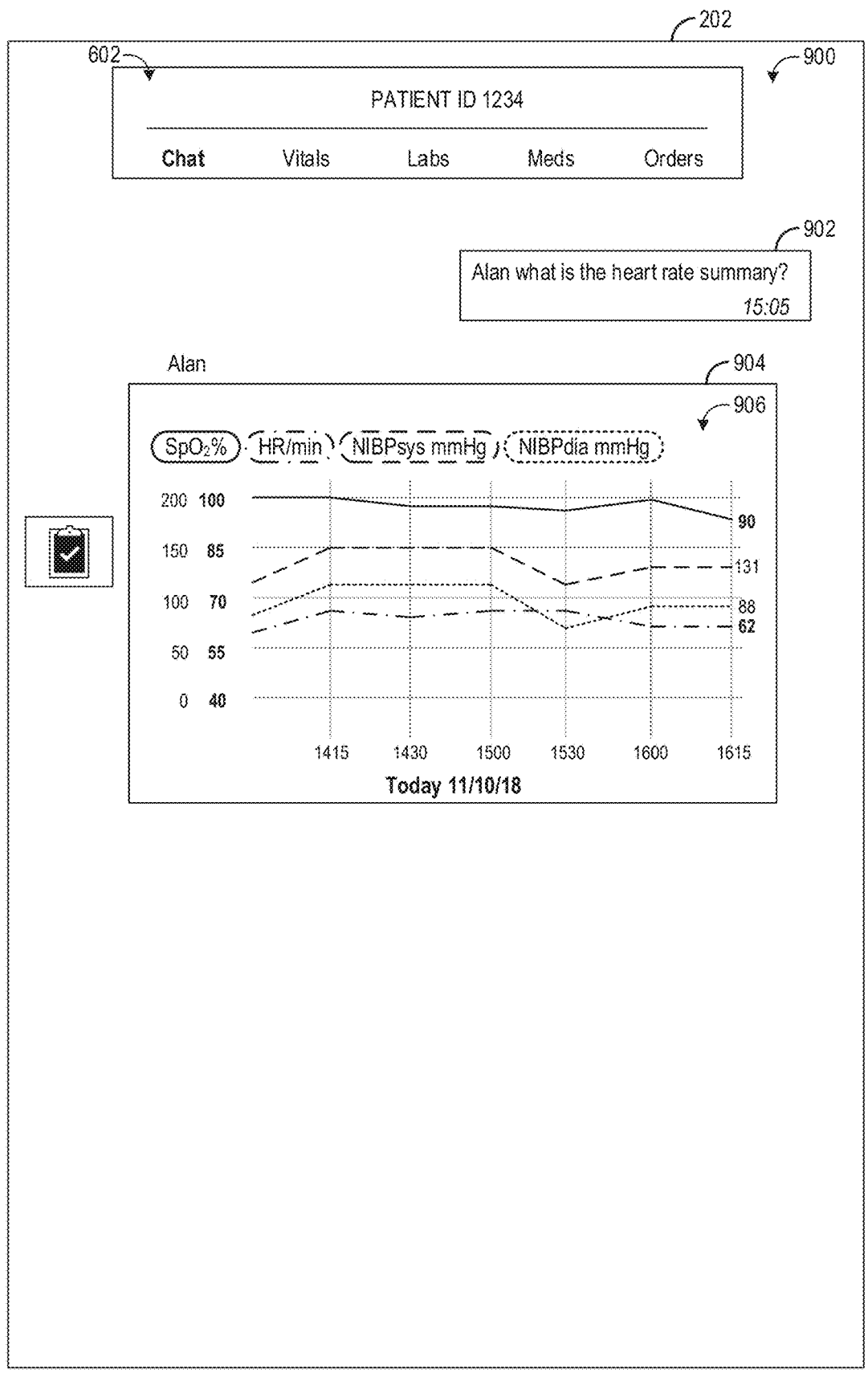

FIG. 9 shows another example communication thread 900 of a patient-specific communication channel, and as such may be a non-limiting example of communication thread 104 introduced in FIG. 1. Communication thread 900 may be displayed on the display device 602. Communication thread 900 may be displayed in response to a user request to display the communication thread and may include the identification header 604 that identifies the patient being discussed/monitored via the communication thread. In the illustrated example, communication thread 900 is specific to patient ID 1234. In the illustrated portion of communication thread 900, communication is occurring between a care provider (e.g., Dr. Smith) and the virtual healthcare assistant ("Alan"). Communication thread 900 is being viewed by Dr. Smith, although any authenticated/approved user may view communication thread 900.

Similar to communication thread 700 and communication thread 800, communication thread 900 includes a request from Dr. Smith to view multiple medical parameters, in the form of message 902. The virtual assistant may process the natural language in the message 902 (e.g., what is the heart rate summary) to determine that trend graphs for medical parameters related to patient heart rate (e.g., heart rate, blood pressure, and oxygen saturation) have been requested. The virtual assistant may obtain data sets for each requested medical parameter from the patient's EMR. For example, the virtual assistant may obtain a first data set that includes patient heart rate over a duration (e.g., the prior two hours), a second data set that includes patient oxygen saturation (SpO2) over the duration, and a third data set that includes patient blood pressure (both systolic and diastolic) over the duration. The virtual assistant may then plot each data set on the same graph, in order to generate the single graph 906 that is then output as a message 904 in the communication thread.

In the example shown in FIG. 9, graph 906 includes two y-axes, a first y-axis having a first range of values (0-200, shown as non-bolded text) and a second y-axis having a second range of values (40-100, shown as bolded text). The first y-axis is the y-axis for the plots of systolic blood pressure and diastolic blood pressure, while the second y-axis is the y-axis for the plot of SpO2 and heart rate. By including more than one y-axis even though the plotted values for all the plots overlap, different plots may have different scales, enabling changes in each plot to be visualized at a scale that is relevant for patient care. For example, the scaling shown in graph 906 may allow for relatively small changes in the SpO2 plot to be more easily visualized, given that the changes in the SpO2 plot may be important for patient care decisions. In contrast, changes to systolic blood pressure may be relatively larger and/or small changes in diastolic blood pressure may be of less importance for patient care decisions, and so the scaling of the y-axis for the plots of systolic blood pressure and diastolic blood pressure does not magnify small changes. As an example, if instead the y-axis for the plots of systolic blood pressure and diastolic blood pressure were scaled to magnify small changes in the blood pressure data, the resulting plots may obscure the more clinically relevant changes in the SpO2 plot.

Thus, a virtual assistant may be configured to generate a single graph showing multiple, different medical parameters for a patient in response to a request from a user (e.g., a care provider) entered via a communication thread that is specific to the patient. The virtual assistant may generate the graph in a manner that enhances visual clarity of the presented information, as explained above. As such, various aspects of the graph, such as number of y-axes (and the values plotted on those y-axes), segment of time or events plotted on the x-axis, whether some or all y-values are shown in text on the graph, etc., may be selected based on the request. For example, the aspects may be selected based on the number of parameters that are requested, whether the parameters are event-based, time-based, and/or include numeric values, and the type of parameters being requested.

FIG. 10 is a flow chart illustrating a method 1000 for a collaborative healthcare system serving a medical facility, such as a hospital. Method 1000 may be executed by a processor of a computing device (such as processor(s) 132 of server system 102 of FIG. 1) according to instructions stored on a non-transitory memory of the device (e.g., memory 130 shown in FIG. 1) in combination with the various signals received at the server system from components of the collaborative healthcare system (e.g., patient medical data signals from monitoring devices 120, communication from hospital operational systems 118, etc.) and signals sent from the server system to the care provider devices and/or other system components.

At 1002, method 1000 includes receiving a notification that a patient has been admitted to the medical facility. The notification may be received from the hospital operational systems, and may include a patient identifier, patient state (e.g., the condition for which the patient is being admitted), and care provider information. The care provider information may include identifiers of various care providers (such as doctors and nurses) that are currently attending to the patient.

At 1004, method 1000 includes generating a communication channel including a communication thread and a dashboard for the patient. In order to generate the communication channel, verified care providers of the patient (e.g., as indicated by the notification from the hospital operational systems) and one or more virtual healthcare assistants (VHAs) may be joined to the communication channel, as indicated at 1006. The communication channel may facilitate text and/or rich-media based messages to be sent among all the verified care providers and VHAs that are joined to the communication channel. The one or more VHAs may include an EMR VHA, a guideline VHA, a predictive VHA, a listening VHA, a monitoring VHA and/or other VHAs. To join the channel, each VHA may receive a message that a new channel has been opened and the access application (e.g., executing on the server system 102) may add the VHAs to the eligible participants of the channel. Moreover, in some examples, not all available VHAs may be invited to all channels (e.g., a sepsis VHA may not be invited in a non-relevant case or the listening VHA may not be invited due to patient refusal to be monitored by recording).

Generating the dashboard may include configuring the dashboard based on the patient state and/or user settings, as indicated at 1008. As explained previously, a patient dashboard may be a graphical user interface that facilitates display of patient medical information, such as real-time vital signs, medical history, treatment plan, and/or other information. The dashboard may also include relevant/desired messages from the communication thread. Which medical information to display on the dashboard and in what format may be determined based on the patient state (e.g., current medical condition for which the patient is being treated) and/or on user settings, which may be configured by the end-viewer of the dashboard. In this manner, different patients may have different medical information displayed on different dashboards, and different care providers may view different medical information for the same patient, if desired.

At 1010, method 1000 includes receiving text- and/or rich-media-based messages from the participants on the communication channel, including care providers and VHAs. During the course of patient care, care providers may communicate with each other on the communication channel via messages of the communication thread to coordinate care, give care instructions, and/or confirm appropriate care is being carried out. Further, care providers may send requests to the VHAs via the communication thread for various information related to the patient care, including patient medical history, care guidelines, predicted future patient state, recommended lab tests, etc. Further still, VHAs may send notifications via the communication thread of changes in patient state, patient medical history, patient care guidelines, predicted future patient states, lab test status, etc. The messages sent from a care provider may be sent from a care provider device (e.g., device 134) and received at the server system via a suitable connection (e.g., wired or wireless, such as via the Internet). The messages sent from the VHAs may be generated by the VHAs, which may be stored and executed on the server system, the cloud, and/or a remote device. As used herein, messages may refer to any suitable information sent and received on the communication thread, including but not limited to text messages (entered via typing, touch, or stylus input, voice input, or automatically generated by a VHA), images, voice messages (e.g., recordings of voice input), and videos.

At 1012, method 1000 includes distributing the received messages to other participants on the communication channel and saving the received messages as a communication thread. Each message that is sent to the server system may be tagged with various identifiers that identify the sender as well as the patient communication thread to which the message pertains (e.g., the patient identifier). The server system may then send the message to other participants of the communication channel, e.g., the care providers and/or VHAs that did not send the original message, and save the message as part of a saved communication thread. The saved communication thread may then be viewed by other users at other times, retrieved in response to a user request to view some or all of the communication thread, etc. However, in some examples, the device from which the original message was sent (e.g., the care provider device) may send the message to all other participants on the communication channel, and thus the server system may not distribute the message to the other participants.

At 1014, method 1000 includes receiving patient medical information. The patient medical information may be received from one or more patient monitoring devices that are configured to measure patient state and condition, including sensors that measure vital signs (e.g., blood pressure, heart rate, and blood oxygen level), diagnostic imaging modalities, microphones in proximity to the patient, and so forth. Additionally, the patient medical information may be received from the communication thread. For example, two care providers may be messaging each other on the communication thread and exchanging information relating to the patient, such as visual information (e.g., skin pallor, redness, or yellowness) of the patient that may indicative of patient state. One or more of the VHAs may be configured to parse the message and determine that relevant medical information is being exchanged and then save the medical information as messages within the communication thread.

At 1016, method 1000 includes updating a digital twin of the patient with the medical information. The digital twin may be a digital replica/representation of the patient that is saved at the computing device (e.g., digital twin 108 saved on the server system 102). The digital twin may include patient demographic information, medical history, and other information to provide, to the extent possible, a simulation/representation of the current patient medical state. When new or updated medical information is received, the digital twin may be updated to reflect the most recent patient medical state. The digital twin may be accessed (e.g., by one or more of the VHAs) to retrieve patient medical information, predict future patient states (e.g., simulations may be performed using the information stored in the digital twin to determine the probability of the patient developing a certain condition), identify the most relevant lab tests to be conducted to diagnose a patient condition, and provide appropriate context when retrieving care guidelines.

At 1018, method 1000 includes outputting the communication thread for display when prompted. In an example, the prompt may include an explicit request to view the communication thread for the patient, entered by selection of an appropriate link/control button on the patient dashboard or selection of the patient's communication thread from a collaborative interface, as indicated at 1020. For example, a message button may be displayed via the patient dashboard, and selection of the message button may trigger display of the communication thread for that patient. In another example, a patient link may be selected to launch the communication thread from a collaborative system interface. In an example, the communication thread may be output for display automatically in response to a request from one or more of the VHAs, as indicated at 1022. For example, a listening VHA may detect that one or more care providers are discussing a particular piece of the patient's medical history, and the listening VHA may send a portion of the communication thread that includes reference to the particular piece of medical history to the care provider's device for display. In another example, a VHA may detect that a patient vital sign has reached a level that may indicate a potential urgent patient condition and the VHA may output an alert regarding the vital sign on the communication channel. In some examples, issue of such an alert may prompt automatic display of the communication thread on each participant's display device.

At 1024, method 1000 includes outputting the dashboard for display when prompted. In an example, the prompt may include an explicit request to view the dashboard for the patient, entered by selection of an appropriate link/control button on the communication thread or selection of the patient's dashboard from a collaborative interface, as indicated at 1026. For example, as shown in FIG. 2, a link to the dashboard may be displayed in the communication thread, and selecting the link may trigger display of the dashboard for that patient. In an example, the dashboard may be output for display automatically in response to a request from one or more of the VHAs, as indicated at 1028. For example, the listening VHA may detect that a care provider is discussing the patient's current medical state and may automatically output the dashboard for display on the care provider's device so that the care provider may view patient medical information displayed in the dashboard that relates to the current medical state being discussed. Method 1000 then returns.

FIG. 11 is a flow chart illustrating a method 1100 for generating graphs of patient-specific medical data via a virtual healthcare assistant that are then output to a care provider. Method 1100 may be executed by a processor of a computing device (such as processor(s) 132 of server system 102 of FIG. 1) according to instructions stored on a non-transitory memory of the device (e.g., memory 130 shown in FIG. 1). As explained above with respect to FIG. 1, the server system 102 may store/execute one or more virtual healthcare assistants (VHAs) that are configured to perform certain tasks related to providing medical information of the patient to the one or more care providers attending to the patient, as explained below.

At 1102, method 1100 includes receiving a natural language user input. The natural language user input may be input as a message from a care provider, via voice or text, and may include patient-specific information in natural language form. For example, as explained previously, each patient may have a dedicated communication channel including a communication thread that facilitates communication among the care providers treating the patient and one or more VHAs. When a care provider enters a natural language input on the communication thread, the input (e.g., message) may be received at the server system and the input may be processed, via the one or more VHAs, to determine the content of the natural language user input, as indicated at 1104. The one or more VHAs may utilize a speech recognition engine in examples where the natural user input is input via voice. As explained previously, the one or more VHAs may be trained to process natural language inputs to determine the content of the input, e.g., determine if the input includes a request for information, and if the content includes a request for information, the one or more VHAs may be trained to determine which patient the care provider is referring to and what information is being requested. In some examples, each VHA may process a received message to understand (in natural language) the intent of the message and determine if the intent of the message includes a task that the VHA is trained/configured to perform. In some examples, the server system may include a central entity configured to understand the intent of the message (e.g., from the natural language of the message) and determine which VHA is best configured to handle the request. Then, the mapping from intent (and VHAs) to a specific API of a specific VHA is one-to-one, e.g., only one VHA handles a specific intent (or intent-entity combination).

The information request may be an explicit request, where the care provider explicitly asks for certain medical information, such as "please send me the patient's heart rate over the last four hours." In other examples, the request may be implicit. Implicit requests may include assumptions (on the part of the VHAs executing on the server system) that certain medical information may be helpful, such as when a change in patient vital signs is detected, that are not accompanied by an actual request by the care provider.

At 1106, method 1100 determines if the user input includes a request for multiple data sets of patient-specific medical information. As explained above with respect to FIGS. 6-9, a care provider may enter one or more natural language user inputs (e.g., messages on the communication thread) requesting to view two or more different pieces of patient medical information, such as heart rate and blood pressure; oxygen saturation and oxygen flow rate; heart rate, blood pressure, oxygen saturation, and oxygen flow rate; etc. If the user input does not include a request for multiple data sets, for example if the user input includes a request for a single data set (e.g., just heart rate), a request for treatment guidelines or diagnosis guidelines, or if the user input is not directed at the VHA (e.g., the message is intended for another care provider), method 1100 proceeds to 1108 and performs one or more actions as indicated by the user input. For example, if the user input includes a request for a single piece of medical information from the patient's EMR, the VHA (e.g., EMR VHA) may retrieve the information from the patient's EMR and output the information as a message in the communication thread. Thus, in some examples, performing the one or more actions may include retrieving the requested information, as indicated at 1109, and outputting a message including the information for display via the communication channel, as indicated at 1110. In other examples, the one or more actions may simply include saving/distributing the message (e.g., when the user input does not include any requests for information).

If the user input does include a request for multiple data sets of patient-specific medical information, method 1100 proceeds to 1112 to generate, with a VHA, a single graph plotting two or more data sets. As an example, the user input may include a request to view patient heart rate and blood pressure trends. Thus, a VHA (such as the EMR VHA, in examples where multiple VHAs are available) may generate a single graph that includes a first plot of heart rate over a duration and a second plot of blood pressure over the duration.

To generate the single graph, the data sets are obtained from the patient's EMR, as indicated at 1114. For example, each blood pressure measurement over the duration (e.g., 4, 8, 12, 24 hours or longer) that is stored in the patient's EMR (and/or digital twin) may be retrieved by the VHA, as well as each heart rate measurement over the duration that is stored in the patient's EMR (and/or digital twin). The multiple data sets are then plotted on the single graph based on one or more overlapping parameters, as indicated at 1118. The one or more overlapping parameters may include aspects of the multiple data sets that are common among the data sets, or at least have values that are common or overlap. For example, the overlapping parameter may include time. Other examples of overlapping parameters may include data value ranges (e.g., each data set may have data values that are included in a common range of values), events (e.g., medicine administration may be time-based and/or may be event-based, where each administration event is time-stamped and/or event-stamped (e.g., first administration, second administration, etc.)), or other parameters. The data sets may be plotted according to the overlapping parameter(s) by setting one of the axes of the graph as the overlapping parameter, at least in some examples (e.g., the data sets may be plotted as a function of time, with overlapping time duration plotted on the x-axis). In other examples, the overlapping parameter may include a data range of the y-axis, with the overlapping data value range being plotted on the y-axis).

In the example of the heart rate and blood pressure data sets, the heart rate and blood pressure data sets may include at least two overlapping parameters, time and data value ranges. For example, referring to graph 706 of FIG. 7, both the heart rate data set and blood pressure data set may include a plurality of values each measured at specific times, where each measured value is stored with the time/date that the value was measured. In this way, each of the blood pressure and heart rate data sets may be plotted as a function of time, as shown in FIG. 7. Further, each of the heart rate and blood pressure data sets may include values within an overlapping range, e.g., between 40 and 130. Accordingly, in one example, the two data sets may plotted on the single graph with a common x-axis (e.g., representing time) and a common y-axis (e.g., representing both heart values and blood pressure values). However, doing so may obscure important but relatively smaller changes in heart rate, given that heart rate may include a narrower range of values than blood pressure (e.g., between approximately 60 and 100 for heart rate and between approximately 50 and 130 for blood pressure). Thus, as shown in FIG. 7, the heart rate and blood pressure data sets may be plotted with different y-axes having different scales (e.g., 40-160 for blood pressure and 40-100 for heart rate).

The decision on which overlapping parameter(s) to include as common values for the different plots and which overlapping parameter(s) not to include as common values may be based on the type of medical information being plotted. For example, each different type of medical information (e.g., heart rate, blood pressure, temperature, oxygen saturation, medicine dosage) may be associated with an allowed scale. For example, heart rate may have an allowed scale of 20% the minimum and maximum plotted values (e.g., such that the scale can start at a value 20% lower than the minimum plotted value and can extend until a value 20% greater than the maximum plotted value, which in the example of FIG. 7 would include a range of approximately 40-120 bpm). Blood pressure may have the same allowed scale, or may have a different allowed scale. If the allowed scales do not fully overlap, the data sets may be plotted with different y-axes.

In other examples, the allowed scales may be based on the difference between the minimum and maximum plotted values for each data set, a desired magnification of the difference in the minimum and maximum plotted values, or other suitable parameter(s). Further, the scales of the y-axes, as well as the number of plotted data points, may be based on a size of the graph, which may be predetermined (e.g., each graph that is output in the communication thread may have the same size) or may be based on the number of data sets being plotted, type of data being plotted, etc.

Thus, in some examples, generating the single graph may include adjusting the scale of one or more of the plots of the single graph, as indicated at 1118. Adjusting the scale may include selecting a scale for each plot, as described above. In some examples, adjusting the scale may include generating the single graph with the two or more plots, and then adjusting the scale of one or more of the plots to remove portions of the y-axis, for example, that do not convey information. In some examples, each data set may be plotted on a common y-axis having a scale selected to accommodate all of the plotted values, and then the VHA may be configured to identify the displayed magnitude of variance for each plot, where the displayed magnitude of variance includes, for each plot, the difference between the maximum value and minimum value as a proportion of the overall range of values. For example, if the blood pressure and heart rate illustrated in graph 706 of FIG. 7 were plotted on a common y-axis having a range of 40-140 (which would accommodate all plotted values), the heart rate plot may have a displayed magnitude of variance of 0.35 (97–62/100) while the systolic and diastolic blood pressure plots may have magnitudes of variance of 0.17 (123–106/100) and 0.18 (68–50/100), respectively. The VHA may then determine that the magnitude of variance for the heart rate plot is not as high as desired, and thus the VHA may adjust the graph to include the two different y-axes as shown in FIG. 7 (where the heart rate plot has a magnitude of variance of 0.58 (97–62/60).

In some examples, it may be difficult to plot all the requested data sets on the single graph and maintain sufficient visual clarity of each plot. Accordingly, in some examples, as indicated at 1120, an additional graph may be generated and/or some of the plotted data may be selectively visualized. For example, if three or more data sets are requested and/or if some of the data sets cannot be aligned, two graphs may be generated, or some data may be visualized only when a user requests to view the hidden data. For example, if a care provider requests to view the heart rate summary shown in FIG. 9 along with respiration rate and body temperature, a single graph having all the requested plots may potentially obscure data of significance and/or force some data sets to be plotted on a y-axis having a larger than desired range. In such examples, two (or more) graphs may be generated. In an example, the VHA may generate the graph in the manner described above, and if after following the rules regarding the allowed scales/overlapping parameters, the VHA determines that more than two or three y-axes are indicated, the VHA may generate two graphs instead of one.

Figure 15A:
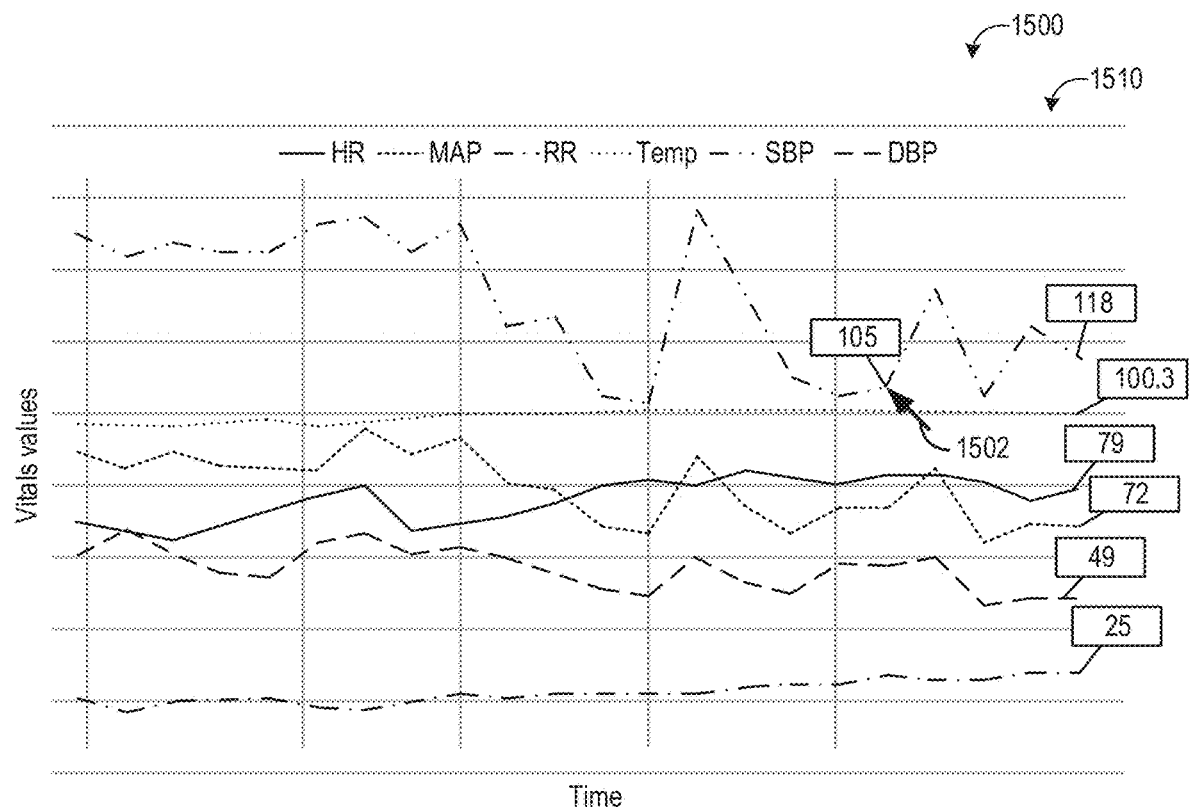
FIGS. 15A and 15B show an example multi-parameter graph that may be output as part of a communication occurring on a communication channel of the collaborative healthcare system.
Figure 15B:
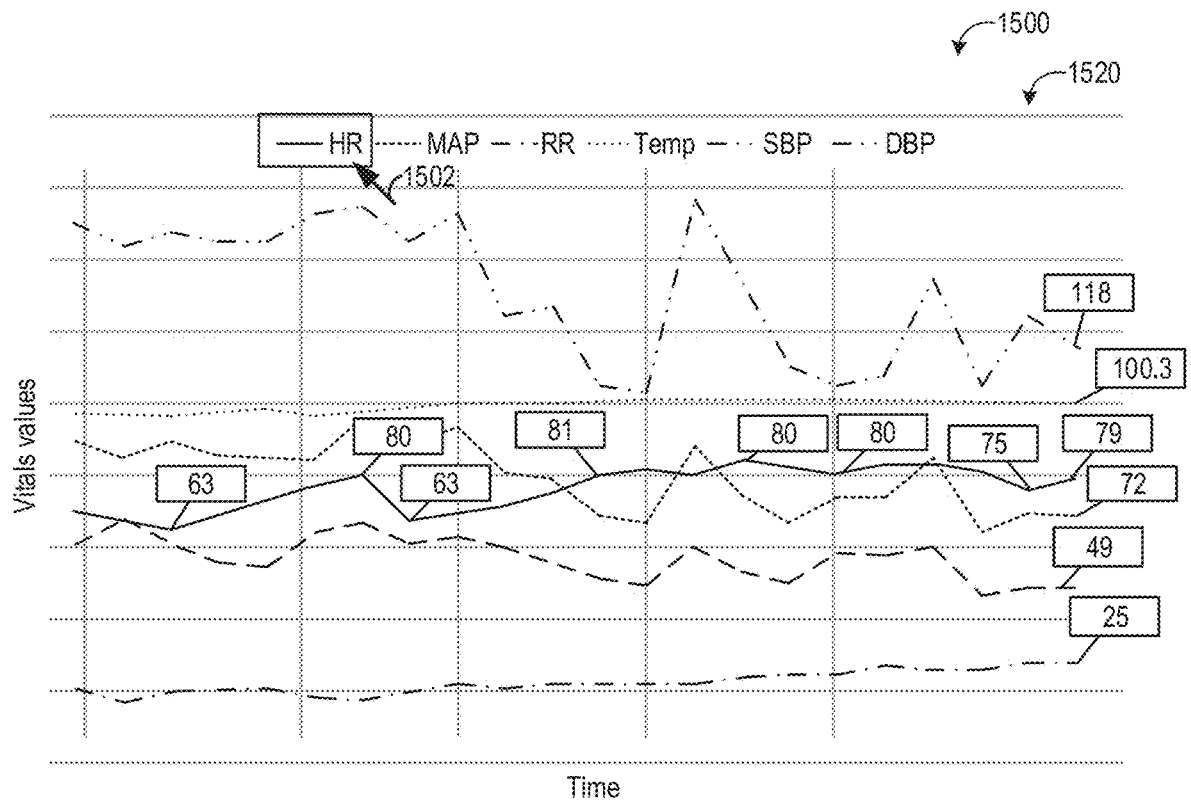

FIGS. 15A and 15B show an example multi-parameter graph 1500 that may be displayed as part of a communication thread, such as one of the communication threads discussed above with respect to FIGS. 7-9. FIG. 15A shows the multiple-parameter graph 1500 in a first state 1510 and FIG. 15B shows the multi-parameter graph 1500 in a second state 1520. The graph 1500 includes plots of six different data sets: heart rate (HR), mean arterial pressure (MAP), respiration rate (RR), temperature, systolic blood pressure (SBP), and diastolic blood pressure (DBP). The six different data sets are plotted as a function of time and on a common y-axis, with values spanning 0-160. It is to be understood that no units are indicated for the values on the y-axis, since the units are different among the different data sets (e.g., beats per minute for HR, degrees F. for temperature, etc.). The final plotted value for each data set is shown on the graph in numeric text format (e.g., 118 for SBP, 100.3 for temperature, 79 for HR, 72 for MAP, 49 for DBP, and 25 for RR).

Because each data set is plotted on the same y-axis, the values for the y-axis span a wide range (e.g., 0-160), which may make it difficult to discern precise values for some or all of the data points plotted on the graph. Accordingly, a user may select one or more data points to view the y-value for that data point. As shown in FIG. 15A, the user has entered an input selecting a data point on the SBP curve (e.g., the user has moved a cursor 1502 over the data point and in some examples clicked a mouse or otherwise indicated that the user wants to view the data point in more detail), and in response, the y-value for that data point is displayed (e.g., SBP of 105).

FIG. 15B shows the graph 1500 in the second state 1520, where the user has entered an input selecting the HR curve (e.g., the user has moved the cursor 1502 over the HR legend and in some examples clicked a mouse or otherwise indicated that the user wants to view the curve in more detail), and in response, a plurality of y-values for that curve are displayed (e.g., eight different y-values for HR at various time points are displayed).

In this way, a large amount of data, including many different data sets having different units, scales of values, and so forth, may be plotted on a single graph. To enhance visualization of the data without cluttering the graph and obscuring underlying data, one or more data points may be selectively visualized via a user selection of those data points or user selection of an entire curve. As used herein, the term selective visualization of data points refers to display of the actual x- and/or y-values of those data points in numeric text format. It is to be understood that at least in some examples, the data points are still visible as points in a graph. For example, referring to FIG. 15A, the selected data point for the SBP curve may be shown as part of the SBP curve, whether or not the data point is selected. Once the data point is selected, the y-value for the data point is also displayed, in numeric text format.

Returning to FIG. 11, at 1122, method 1100 includes outputting the single graph for display via the communication channel. For example, the single graph (and in some examples, the one or more additional graphs) may be formatted as a message and output as part of the communication thread for the patient. Method 1100 then returns.

Thus, method 1100 of FIG. 11 provides for the flexible presentation of aggregate data via a virtual assistant communicating with one or more professionals that interacting with a subject. The virtual assistant may be executed on a central computing device or devices (e.g., a server) and trained to process natural language inputs that are received from one or more client devices (e.g., from one or more devices used by the one or more professionals). The natural language inputs may be processed to determine if the inputs include a user request for information, for example. If the virtual assistant determines that the natural language input includes a user request to view multiple different pieces of record data relating to the subject, the virtual assistant is configured to obtain a plurality of data sets from an electronic record of the subject, each corresponding to one of the requested pieces of record data. The virtual assistant is configured to plot the data sets to generate a single graph plotting the multiple different pieces of record data. The virtual assistant may then output the single graph for display, such as within a communication thread that is viewable on the client devices. In this way, in response to a single request from a user, multiple different data sets may be plotted on the same graph, which may facilitate quick visualization of desired record data in a manner that highlights correlations among the record data, trends of the record data, etc.

As explained above, the one or more professionals may be healthcare providers (e.g., care providers), such as doctors, nurses, etc. The subject may be a patient that is currently being monitored by the healthcare providers. The record data may be medical data of the patient that is stored in an electronic medical record of the patient. The virtual assistant may obtain a plurality of data sets (e.g., each data set including values of a given medical parameter over time or per event) from the patient's EMR and plot each data set on a single graph based on one or more overlapping parameters of the plurality of data sets. The one or more overlapping parameters may include time, data value ranges, events, or other parameters, such that the data sets are plotted according to variables that are the same or overlap. The virtual assistant may follow a set of graphing rules that dictate how many different pieces of record data can be plotted together, the allowable scale of each plotted data set, etc. The graphing rules may be set based on the type of record data being plotted and/or the size of the graph, at least in some examples.

The plurality of data sets/different pieces of record data that are plotted may differ in units, scale, data source, sampling frequency, sampling timing, and/or other parameter. For example, in the graph shown in FIG. 7, a first data set includes a plurality of heart rate values and a second data set includes a plurality of blood pressure values. The heart rate values may be in beats per minute, while the blood pressure values may be in mmHg. Further, the heart rate values may be collected with a first data source (e.g., manually via a healthcare provider) while the blood pressure values may be collected with a second data source (e.g., a blood pressure cuff).

In this way, the virtual assistant described herein may utilize natural language processing to determine the intent of a natural language user input, and then carry out an action based on the intent. The action may include assembling a single graph of different data in an intelligent manner than highlights data or data changes of significance while maintaining visual clarity. The information that is presented via the single graph may include pieces of information that are separately viewable via various interfaces (e.g., a dashboard, vital signs interface, EMR access interface) but otherwise may not be available for aggregate viewing. For example, the heart rate and blood pressure trends shown in FIG. 7 may be separately viewable via the vital signs interface, but may not be viewed together (e.g., on a single screen at the same time) via the vital signs interface. In this way, the communication thread and virtual assistant provide a mechanism via which aggregate medical information may be presented to a care provider with a single user request.

In some examples, the virtual assistant may learn user preferences for displayed data, or otherwise may learn how to present requested data in a format that allows for desired visualization of the requested data. For example, the virtual assistant may output a single graph that is formatted similar to the graph 706 of FIG. 7, where each data point includes an annotation of the y-value for that data point. If a particular care provider provides feedback regarding the graph (such as entering a subsequent input on the communication thread requesting to view the graph again, but without the annotations of the y-values), the virtual assistant may generate and output a graph that is more similar to that shown in FIG. 15A (e.g., where the annotated values are only shown upon user request). The virtual assistant may learn, whether for that care provider or globally, that when three or more curves are shown on a single graph, not to include labels/annotations of the values for the data points that are plotted. In another example, after viewing a graph generated and output by the virtual assistant, a user may enter input to the communication thread requesting that the graph include more or fewer y-axes, for example, and the virtual assistant may learn that for that combination of requested data, a certain number of y-axes is preferred. In still further examples, the manner in which requested data is plotted and presented may be set by user preferences and/or administration preferences.

In some examples, such as the example illustrated in FIG. 9, the request for multiple different pieces of data may include a request for a summary of a condition or aspect of the subject, such as the request for the heart rate summary shown in FIG. 9. As explained above, in response to the request for the heart rate summary, the virtual assistant may assemble a graph that includes multiple plots of different data sets all related to heart rate, including heart rate, and also including blood pressure and oxygen saturation. In this way, multiple different types of information may be presented together in response to a short, single user request, which may expedite the delivery of desired information and reduce user effort required to interact with the communication thread.

FIG. 12 is a flow chart illustrating a method 1200 for generating summaries of patient-specific medical data, via a virtual healthcare assistant, that are then output to a care provider. Method 1200 may be executed by a processor of a computing device (such as processor(s) 132 of server system 102 of FIG. 1) according to instructions stored on a non-transitory memory of the device (e.g., memory 130 shown in FIG. 1). As explained above with respect to FIG. 1, the server system 102 may store/execute one or more virtual healthcare assistants (VHAs) that are configured to perform certain tasks related to providing medical information of the patient to the one or more care providers attending to the patient, as explained below.

At 1202, method 1200 includes receiving a natural language user input. The natural language user input may be input as a message from a care provider, via voice or text, and may include patient-specific information in natural language form. For example, as explained previously, each patient may have a dedicated communication channel including a communication thread that facilitates communication among the care providers treating the patient and one or more VHAs. When a care provider enters a natural language input on the communication thread, the input (e.g., message) may be received at the server system and the input may be processed, via the one or more VHAs, to determine the content of the natural language user input, as indicated at 1204. The one or more VHAs may utilize a speech recognition engine in examples where the natural user input is input via voice. As explained previously, the one or more VHAs may be trained to process natural language inputs to determine the content of the input, e.g., determine if the input includes a request for information, and if the content incudes a request for information, the one or more VHAs may be trained to determine which patient the care provider is referring to and what information is being requested. In some examples, each VHA may process a received message to understand (in natural language) the intent of the message and determine if the intent of the message includes a task that the VHA is trained/configured to perform. In some examples, the server system may include a central entity configured to understand the intent of the message (e.g., from the natural language of the message) and determine which VHA is best configured to handle the request. Then, the mapping from intent (and VHAs) to a specific API of a specific VHA is one-to-one, that is, only one VHA handles a specific intent (or intent-entity combination).

The information request may be an explicit request, where the care provider explicitly asks for certain medical information, such as "please send me the patient's heart rate over the last four hours." In other examples, the request may be implicit. Implicit requests may include assumptions (on the part of the VHAs executing on the server system) that certain medical information may be helpful, such as when a change in patient vital signs is detected, that are not accompanied by an actual request by the care provider.

At 1206, method 1200 determines if the user input includes a request for a patient condition summary. A care provider may enter one or more natural language user inputs (e.g., messages on the communication thread) requesting to view a patient condition summary, such as the heart rate summary shown in FIG. 9. If the user input does not include a request a patient condition summary, for example if the user input includes a request for a single data set (e.g., just heart rate), a request for treatment guidelines or diagnosis guidelines, or if the user input is not directed at the VHA (e.g., the message is intended for another care provider), method 1200 proceeds to 1208 and performs one or more actions as indicated by the user input. For example, if the user input includes a request for a single piece of medical information from the patient's EMR, the VHA (e.g., EMR VHA) may retrieve the information from the patient's EMR and output the information as a message in the communication thread. Thus, in some examples, performing the one or more actions may include retrieving the requested information, as indicated at 1209, and outputting a message including the information for display via the communication channel, as indicated at 1210. In other examples, the one or more actions may simply include saving/distributing the message (e.g., when the user input does not include any requests for information).

If the user input does include a request for a patient condition summary, method 1200 proceeds to 1212 to generate, with a VHA, a list of medical parameters associated with the patient condition. As an example, the user input may include a request to view a heart rate summary. Thus, a VHA (such as the EMR VHA, in examples where multiple VHAs are available) may generate a single graph that includes a plots of heart rate, blood pressure, and oxygen saturation over a given duration. As another example, the user input may include a request to view a fever summary. In response, a VHA may generate a list of the most recently obtained medical parameters related to fever, such as temperature, heart rate, blood pressure, and so forth.

To generate the list of patient medical parameters, the medical parameters are obtained from the patient's EMR (and/or digital twin), as indicated at 1214. For example, the most recent temperature measurement, heart rate measurement, and blood pressure measurement that are stored in the patient's EMR (and/or digital twin) may be retrieved by the VHA. The parameters that are included in the list of parameters may be predefined by a user or by an administration official, as indicated at 1216. For example, the user requesting the information (e.g., the care provider) may customize which parameters are included in the summary. In other examples, the medical facility may determine which parameters are included in each different patient condition summary. The parameters that may be included in a summary include medical data obtained from monitoring devices (e.g., heart rate, blood pressure, temperature), assessed patient states (e.g., energy level, skin color, cognition), diagnostic imaging results, lab test results, and/or medications (e.g., dosage, timing), each of which are determined to relevant to the patient condition. Further, in some examples, the summary may include only the most recently-obtained values for each parameter. In other examples, the summary may include trends (e.g., graphs) for one or more of the parameters. Whether the summary includes the most-recently obtained values or the trends may depend on user preference, administration preference, type of parameters included in the summary, and/or the patient condition associated with the summary.

At 1218, method 1200 includes outputting the list of medical parameters for display via the communication channel. For example, the list of medical parameters may be formatted as a message and output as part of the communication thread for the patient. As explained above, in some examples, rather than generate a text-based list, the virtual assistant may generate a graph, which may also be output as a message in the communication thread. Method 1200 then returns.

Figure 13:
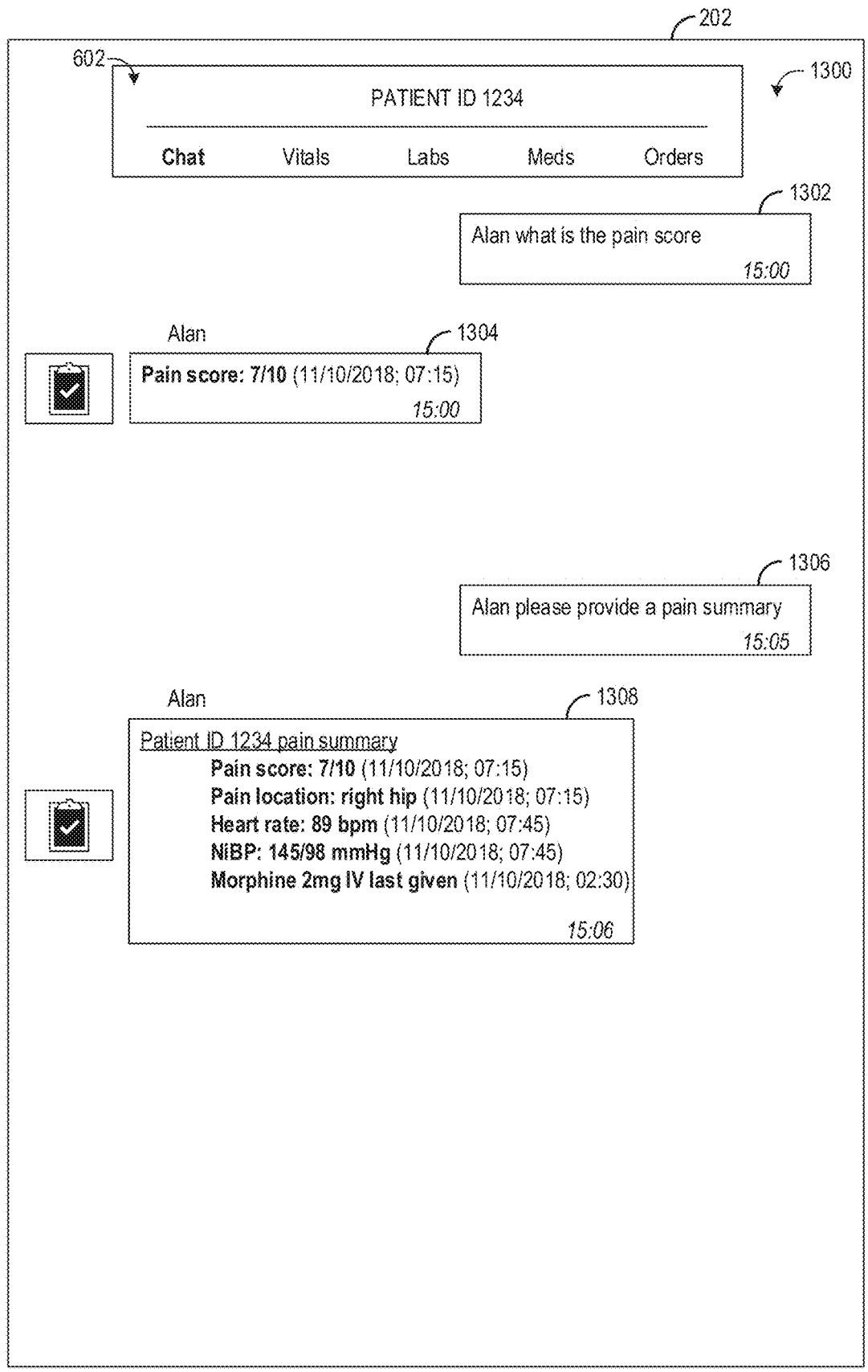
FIGS. 13 and 14 show an example display device displaying further communication threads occurring on a communication channel of the collaborative healthcare system.

FIG. 13 shows another example communication thread 1300 of a patient-specific communication channel, and as such may be a non-limiting example of communication thread 104. Communication thread 1300 may be displayed on the display device 602. Communication thread 1300 may be displayed in response to a user request to display the communication thread and may include the identification header 604 that identifies the patient being discussed/monitored via the communication thread. In the illustrated example, communication thread 1300 is specific to patient ID 1234. In the illustrated portion of communication thread 1300, communication is occurring between a care provider (e.g., Dr. Smith) and the virtual healthcare assistant ("Alan"). Communication thread 1300 is being viewed by Dr. Smith, although any authenticated/approved user may view communication thread 1300.

A first message 1302 of the communication thread 1300 includes a request from Dr. Smith to the virtual assistant to view a pain score for the patient. The virtual assistant receives the message, processes the natural language of the message to determine the intent of the message, and responds with a second message 1304 that includes the requested pain score. In this way, in response to a request for a single item of medical information (e.g., what is the pain score), the virtual assistant responds with only that item of medical information.

A third message 1306 of the communication thread 1300 includes a request from Dr. Smith to view a pain summary for the patient. The virtual assistant receives the message, processes the natural language of the message to determine the intent of the message, and responds with a fourth message 1308 that includes the requested pain summary, which includes a list of patient medical parameters relevant to the patient's pain. As shown, the pain summary includes a most-recently stored pain score, a most-recently stored pain location, a most-recently stored heart rate, a most-recently stored blood pressure, and information regarding a relevant pain medication, herein morphine. The information regarding the medicine includes dosage amount, delivery mechanism, and timing of the last given dosage.

Figure 14:
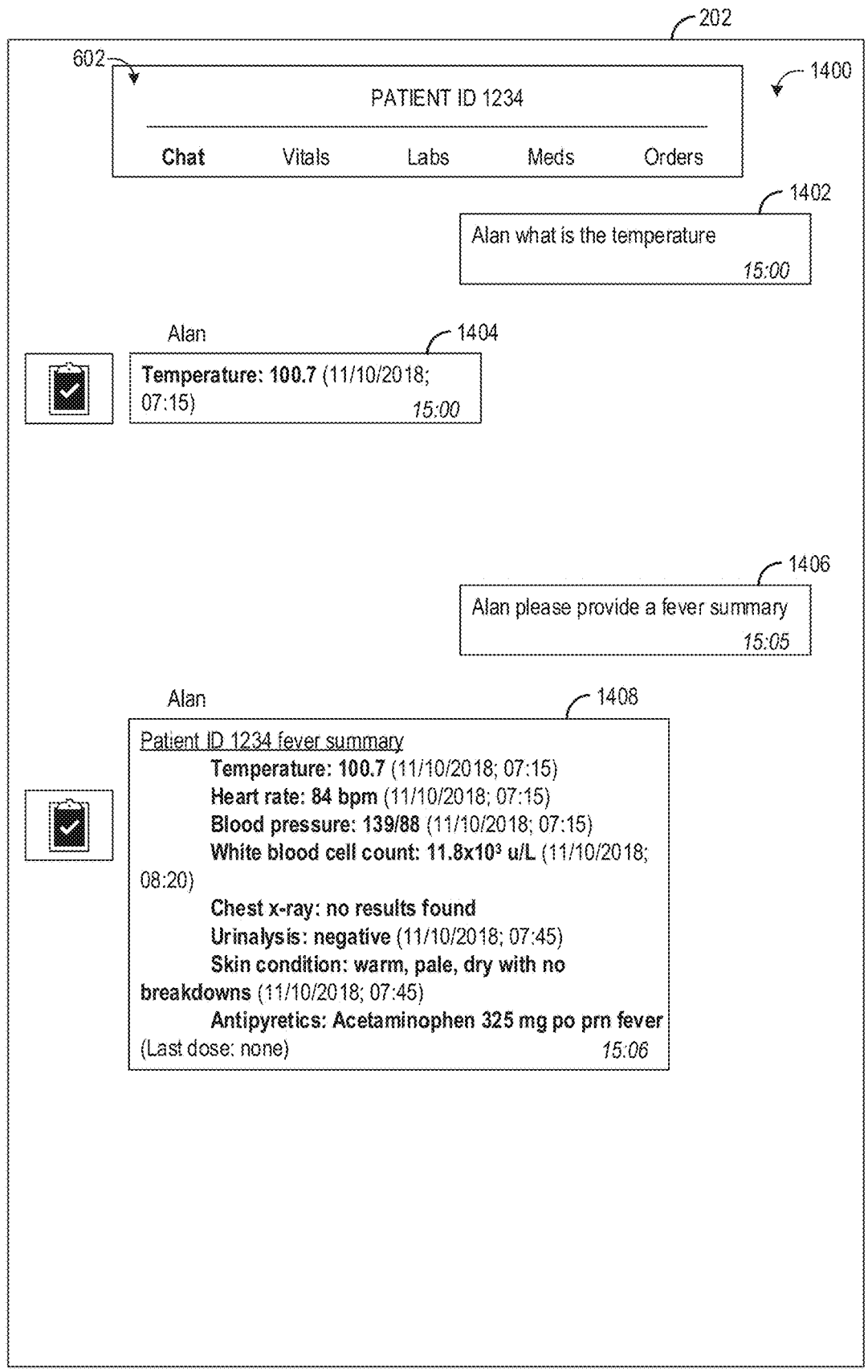

FIG. 14 shows another example communication thread 1400 of a patient-specific communication channel, and as such may be a non-limiting example of communication thread 104. Communication thread 1400 may be displayed on the display device 602. Communication thread 1400 may be displayed in response to a user request to display the communication thread and may include the identification header 604 that identifies the patient being discussed/monitored via the communication thread. In the illustrated example, communication thread 1400 is specific to patient ID 1234. In the illustrated portion of communication thread 1400, communication is occurring between a care provider (e.g., Dr. Smith) and the virtual healthcare assistant ("Alan"). Communication thread 1400 is being viewed by Dr. Smith, although any authenticated/approved user may view communication thread 1400.

A first message 1402 of the communication thread 1400 includes a request from Dr. Smith to the virtual assistant to view a temperature of the patient. The virtual assistant receives the message, processes the natural language of the message to determine the intent of the message, and responds with a second message 1404 that includes the requested temperature. In this way, in response to a request for a single item of medical information (e.g., what is the temperature), the virtual assistant responds with only that item of medical information.

A third message 1406 of the communication thread 1400 includes a request from Dr. Smith to view a fever summary for the patient. The virtual assistant receives the message, processes the natural language of the message to determine the intent of the message, and responds with a fourth message 1408 that includes the requested fever summary, which includes a list of patient medical parameters relevant to the patient's fever. As shown, the fever summary includes a most-recently stored temperature, a most-recently stored heart rate, a most-recently stored blood pressure, the results from a most-recently conducted lab test for white blood cell count, the results from a most-recently conducted chest x-ray, the results from a most-recently conducted lab test for urinalysis, the results from a most-recently conducted assessment for patient skin condition, and information regarding a relevant medication, herein acetaminophen. The information regarding the medicine includes dosage amount, delivery mechanism, and timing of the last given dosage.

The technical effect of generating communication channels including communication thread-dashboard pairs for each patient is to facilitate communication among care providers of the patient and allow virtual healthcare assistants to provide information retrieval and patient monitoring duties, thereby reducing care provider work load, increasing communication among care providers to avoid redundant or missed care of the patient, and allowing the communication occurring on the channel to be saved in a central location accessible by the care providers. By saving the communication on the channel, patient medical state, care decisions, and more may be viewable at a later time in context. The saved communication on the communication channel may be used to auto-populate medical records, reports, or other forms, and may be available for larger-scale (e.g., hospital-wide) analytics on treatment guidelines and patient outcomes.

In another representation, a system includes a display and a computing device operably coupled to the display and storing instructions executable to output, to the display, a patient-specific communication thread including communication among one or more care providers monitoring a patient and a virtual healthcare assistant. Responsive to a request from a user, the instructions are further executable to generate, with the virtual healthcare assistant, a single graph including at least two different plots of medical data specific to the patient, the at least two different plots of medical data plotted from at least two different medical data sets, one or more aspects of the single graph selected based on an overlapping parameter for each of the at least two different medical data sets. The instructions are executable to output, to the display, the single graph, the single graph displayed as part of the communication thread. In a first example of the system, the request is a first request and the instructions are executable to, responsive to a second request from the user, output to the display a patient-specific medical data interface including a predefined list of current medical data parameters of the patient, where the two different plots of medical data are not displayed in the single graph on the medical data interface. In a second example of the system, which optionally includes the first example, one or more of the two different plots of medical data are individually viewable via the medical data interface. In a third example of the system, which optionally includes one or both of the first and second examples, the at least two different plots of medical data differ in a type of medical data being plotted, units of the medical data being plotted, scale of the medical data being plotted, frequency and/or timing at which the medical data was sampled, and/or medical data source via which the medical data was obtained. In a fourth example of the system, which optionally includes one or more or each of the first through third examples, the instructions are executable to, if the request from the user includes a request to view more than three different plots of medical data: generate, with the virtual healthcare assistant, the single graph including two or three of the more than three different plots of medical data and generate an additional graph including any remaining plots of medical data of the three or more different plots of medical data; and output, to the display, the single graph and the additional graph. In a fifth example of the system, which optionally includes one or more or each of the first through fourth examples, the request from the user includes a natural language user input, wherein the virtual assistant is trained to process the natural language user input to determine the request, the training based on one or more deep learning models that map a plurality of natural language inputs to intents and entities, the intents including a plurality of user requests and the entities including a plurality of actions to be performed for the plurality of user requests. In a sixth example of the system, which optionally includes one or more or each of the first through fifth examples, the overlapping parameter is time.

In another representation, a system includes a display and a computing device operably coupled to the display and storing instructions executable to: output, to the display, a patient-specific communication thread including communication among one or more care providers monitoring a patient and a virtual healthcare assistant; responsive to user input requesting a summary of a patient condition of the patient, generate, with the virtual healthcare assistant, a list of patient medical parameters associated with the patient condition; and output, to the display, the list of patient medical parameters associated with the patient condition. In a first example of the system, the list of patient medical parameters comprises one or more current vital signs of the patient relevant to the patient condition, one or more medications previously or currently administered to the patient relevant to the patient condition, and/or one or more assessed patient states relevant to the patient condition. In a second example of the system, which optionally includes the first example, the virtual healthcare assistant is configured to retrieve the list of patient medical parameters from an electronic medical record of the patient, wherein at least two of the patient medical parameters in the list of patient medical parameters are retrieved from different organizational locations of the electronic medical record. In a third example of the system, which optionally includes one or both of first and second examples, the list of patient medical parameters is output to the display as part of the communication thread. In a fourth example of the system, which optionally includes one or more or each of the first through third examples, the instructions are further executable to: responsive to a second user request to view a single patient medical parameter from the list of patient medical parameters, retrieve, with the virtual assistant, the single patient medical parameter; and output, to the display, a visual representation of the single patient medical parameter. In a fifth example of the system, which optionally includes one or more or each of the first through fourth examples, the visual representation of the single patient medical parameter is displayed as part of the communication thread. In a sixth example of the system, which optionally includes one or more or each of the first through fifth examples, the visual representation of the single patient medical parameter is displayed as part of a patient-specific medical data interface, wherein an entirety of the list of patient medical parameters is not viewable via the patient-specific medical data interface.

In another representation, a method includes generating a plurality of patient-specific communication channels, wherein each channel comprises a patient-specific dashboard and a patient-specific communication thread; and for a selected communication channel: outputting a least a portion of the communication thread of the selected communication channel to a display, the communication thread including communication between a care giver monitoring a subject and a virtual healthcare assistant; and responsive to a request entered via the communication thread, outputting a single graph to the display, the single graph including at least two different plots of medical data of the patient, the at least two different plots of medical data plotted from at least two different medical data sets of the patient, one or more aspects of the single graph selected based on an overlapping parameter for each of the at least two different medical data sets. In a first example of the method, the method further includes receiving a natural language user input via the communication thread; processing the natural language user input to determine that the natural language user input includes the request, the request including a request to view the at least two different plots of medical data; and generating the single graph based on the processed natural language user input. In a second example of the method, which optionally includes the first example, the overlapping parameter is a period of time and the one or more aspects of the single graph that are selected based on time include a first data range of a first medical data set of the at least two different medical data sets and a second data range of a second medical data set of the at least two different medical data sets, the first data range and the second data range including data sampled during the period of time. In a third example of the method, which optionally includes one or both of the first and second examples, the method further includes, responsive to a second request, outputting the dashboard of the selected communication channel to the display, wherein one or more of the at least two different medical data sets are individually viewable via the dashboard. In a fourth example of the method, which optionally includes one or more or each of the first through third examples, the at least two different medical data sets are each associated with the patient, and wherein each of the at least two different medical data sets are stored in an electronic medical record of the patient.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:
    a display; and
    a computing device operably coupled to the display and storing instructions executable to:
        output, to the display, a subject-specific communication thread including communication among a virtual assistant and one or more professionals interacting with a subject;
        receive a natural language user input, input via text or voice;
        process, with the virtual assistant, the natural language user input to determine a user request;
        in response to determining that the user request includes a request to display at least two different plots of record data specific to the subject, generate, with the virtual assistant, a single graph including the at least two different plots of record data based on the processed natural language user input, the at least two different plots of record data plotted from at least two different record data sets, one or more aspects of the single graph selected based on an overlapping parameter for each of the at least two different record data sets; and
        output, to the display, the single graph as part of the communication thread, where display of the single graph is dynamically adjusted based on one or more differences between the at least two different record data sets, the one or more differences including differences in units, scale, sampling frequency, sampling timing, and/or record data source.

2. The system of claim 1, wherein the natural language user input is a first natural language user input and the user request is a first user request and wherein the instructions are further executable to:
    receive a second user input;
    process, with the virtual assistant, the second user input to determine a second user request;
    in response to determining that the second user request includes a request to display a subject-specific record data interface, output, to the display, the record data interface, where the record data interface includes a predefined list of record data parameters of the subject and where the single graph is not viewable via the record data interface.

3. The system of claim 2, wherein one or more of the at least two different plots of record data are individually viewable via the record data interface.

4. The system of claim 1, wherein the virtual assistant is trained to process the natural language user input to determine the user request, the training based on one or more deep learning models that map a plurality of natural language inputs to at least one of intents and entities, the intents including a plurality of user requests and the entities including a plurality of actions to be performed for the plurality of user requests.

5. The system of claim 1, wherein the dynamic adjustment of the display of the single graph includes:
    plotting each record data set on a common y-axis having a scale selected to accommodate all plotted values of the at least two record data sets;
    determining a magnitude of variance of each record data set as plotted on the common y-axis; and
    determining that the magnitude of variance for a first record data set of the at least two record data sets is lower than a threshold, and in response, dynamically adjusting the display of the single graph to include a different y-axis for the first record data set.

6. The system of claim 1, wherein the instructions are executable to, if the user request includes a request to view more than three different plots of record data:
    generate, with the virtual assistant, the single graph including two or three of the more than three different plots of record data and generate an additional graph including any remaining plots of record data of the three or more different plots of data; and
    output, to the display, the single graph and the additional graph as part of the communication thread, where the three or more different plots of record data are plotted from three or more different record data sets.

7. The system of claim 1, wherein the overlapping parameter is time, and wherein the dynamic adjustment of display of the single graph is carried out according to a set of rules, the set of rules selected based on the type of record data being plotted and/or a display size of the single graph.

8. A system, comprising:
a display; and
a computing device operably coupled to the display and storing instructions executable to:
   output, to the display, a subject-specific communication thread including communication among a virtual assistant and one or more professionals interacting with a subject, the communication thread including text-based and voice-based messages sent between the one or more professionals and the virtual assistant, the voice-based messages displayed in the communication thread in a text format through a speech recognition engine;
   receive a natural language user input, input via text or voice;
   process, with the virtual assistant, the natural language user input to determine a single user request;
   responsive to determining that the single user request includes a request to view a record data summary specific to an aspect of the subject, select one or more unrequested record data sets and another record data set of the subject, each related to the aspect of the subject, the one or more unrequested record data sets and the other record data set automatically selected from a plurality of record data sets of the subject;
   generate, with the virtual assistant, the record data summary including visual representations of the one or more unrequested record data sets and the other record data set of the subject; and
   output, to the display, the record data summary within the communication thread.

9. The system of claim 8, wherein the virtual assistant is trained to process the natural language user input to determine the user request, the training based on one or more deep learning models that map a plurality of natural language inputs to intents and entities, the intents including a plurality of user requests and the entities including a plurality of actions to be performed for the plurality of user requests.

10. The system of claim 8, wherein the virtual assistant is configured to retrieve each record data set from an electronic record of the subject based on the processed natural language user input, and wherein at least two record data sets are retrieved from different organizational locations of the electronic record.

11. The system of claim 10, wherein the instructions are further executable to:
   receive a second natural language user input, input via text or voice;
   process, with the virtual assistant, the second natural language user input to determine a second user request;
   responsive to determining that the second user request includes a request to view one portion of a record data set of the record data summary, retrieve, with the virtual assistant, the one portion of the record data set based on the processed second natural language user input; and
   output, to the display, a visual representation of the one portion of the record data set.

12. The system of claim 11, wherein the visual representations of the one portion of the record data set is displayed as part of the communication thread.

13. The system of claim 11, wherein the visual representation of the one portion of the record data set is displayed as part of a subject-specific record data interface that includes a predefined list of record data parameters of the subject.

14. A method, comprising:
generating a plurality of subject-specific communication channels, wherein each channel comprises a subject-specific dashboard and a subject-specific communication thread; and
for a selected communication channel,
   outputting a least a portion of the communication thread of the selected communication channel to a display, the communication thread including communication between a professional interacting with a subject and a virtual assistant; and
   responsive to a request entered via the communication thread, outputting a single graph to the display, the single graph including at least two different plots of record data, the at least two different plots of record data plotted from at least two different record data sets, one or more aspects of the single graph selected based on an overlapping parameter for each of the at least two different record data sets, wherein display of the single graph is dynamically adjusted based on one or more differences between the at least two different record data sets, the one or more differences including differences in units, scale, sampling frequency, sampling timing, and/or record data source.

15. The method of claim 14, further comprising:
receiving a natural language user input via the communication thread;
processing the natural language user input to determine that the natural language user input includes the request, the request including a request to view the at least two different plots of record data; and
generating the single graph based on the processed natural language user input.

16. The method of claim 14, wherein the overlapping parameter is a period of time and wherein the one or more aspects of the single graph that are selected based on time include a first data range of a first record data set of the at least two different record data sets and a second data range of a second record data set of the at least two different record data sets, the first data range and the second data range including record data sampled during the period of time.

17. The method of claim 14, further comprising responsive to a second request, outputting the dashboard of the selected communication channel to the display, wherein one or more of the at least two different record data sets are individually viewable via the dashboard.

18. The method of claim 14, wherein the at least two different record data sets are each associated with the subject, and wherein each of the at least two different record data sets are stored in an electronic record of the subject.

19. The method of claim 14, wherein each of the at least two different record data sets includes numeric values obtained over time, and wherein the dynamic adjustment of the display of the single graph includes dynamically adjusting which record data set is plotted as a curve on both an x-axis and a y-axis of the single graph and which record data is plotted as one or more events on only the x-axis.

20. The method of claim 14, wherein the dynamic adjustment of the display of the single graph includes:
   determining an allowed scale for each record data set based on a type of information included in each record data set;
   if the allowed scale for each record data set overlaps, plotting each record data on a same y-axis of the single graph; and if the allowed scale for each record data set does not overlap, plotting at least one record data set on a different y-axis of the single graph than at least one other record data.

* * * * *